US006399074B1

(12) United States Patent
Roland (10) Patent No.: US 6,399,074 B1
(45) Date of Patent: Jun. 4, 2002

(54) LIVE ATTENUATED SALMONELLA VACCINES TO CONTROL AVIAN PATHOGENS

(75) Inventor: Kenneth L. Roland, St. Louis, MO (US)

(73) Assignee: Megan Health, Inc., St. Louis, MO (US)

( * ) Notice: Subject to any disclaimer, the term of this patent is extended or adjusted under 35 U.S.C. 154(b) by 0 days.

(21) Appl. No.: 09/122,441

(22) Filed: Jul. 24, 1998

(51) Int. Cl.⁷ ..................... A61K 39/02; A61K 39/00; A61K 48/00; C12N 1/20; C12N 15/00

(52) U.S. Cl. ............... 424/200.1; 424/93.2; 424/184.1; 435/252.1; 435/252.3; 435/252.8; 435/320.1

(58) Field of Search ...................... 435/252.1, 252.3, 435/252.8; 424/93.1, 184.1, 200.1

(56) References Cited

U.S. PATENT DOCUMENTS

| 5,110,588 A | 5/1992 | Morona et al. ........... 424/200.1 |
| 5,593,679 A | 1/1997 | van den Bosch ........ 424/247.1 |

FOREIGN PATENT DOCUMENTS

| CA | 1331445 | 8/1994 |
| EP | 0 564 689 B1 | 7/1997 |
| WO | WO97/14782 | 4/1997 |

OTHER PUBLICATIONS

Falt et al. (1996) Microb. Path., vol. 20, 11–30, 1996.*
Viret et al. (1993) Mol. Micro., vol. 7 (2), 239–252, 1993.*
Patent Cooperation Treaty International Search Report for PCT/US99/15842, Feb. 24, 2000.
Roland et al., Abstracts in Immunology, Entry E–85, XP–000867749, Construction and Characterization of a Salmonella typhimurium vaccine strain expressing *Escherichia coli* O78 lipopolysacchande, p. 255, 1997.
Bastin et al., Molecular cloning and expression in *Escherichia coli* K–12 of the rfb gene cluster determining the O antigen of an *E. coli* O111 strain, *Mol. Microbiol.* 5:2223–2231 (1991).
Black et al., Prevention of Shigellosis by a *Salmonella typhi*–*Shigella sonnei* Bivalent Vaccine, *J. Infect. Dis.* 155:1260–1265 (1987).
Collins et al. Molecular Cloning, Characterization, and Nucleotide Sequence of the rfc Gene, Which Encodes an O–Antigen Polymerase of *Salmonella typhimurium*, *J. Bacteriol.* 173:2521–2529 (1991).
Formal et al., Construction of a Potential Bivalent Vaccine Strain: Introduction of *Shigella sonnei* Form I antigen Genes into the galE *Salmonella typhi* Ty21a Typhoid Vaccine Strain, *Infect. Immun.* 34:746–750 (1981).
Galan et al., Cloning and characterization of the asd gene of *Salmoennal typhimurium:* use in stable maintenance of recombinant plasmids in *Salmonella* strains, *Gene* 94:29–35 (1990).

Haraguchi et al., Molecular cloning and expression of the 04 polysaccharide gene cluster from *Escherichia coli, Microb. Pathol.* 6:123–132 (1989).
Haraguchi et al., Genetic characterization of the 04 polysaccharide gene cluster from *Escherichia coli, Microb. Pathol.* 10:351–361 (1991).
Hassan et al. Development and Evaluation of an Experimental Vaccination Program Using a Live Avirulent *Salmonella typhimurium* Strain To Protect Immunized Chickens against Challenge with Homologous and Heterologous *Salmonella* Serotypes, *Infect. Immun.* 62:5519–5527 (1994).
Hassan et al., Control of Colonization by Virulent *Salmonella Typhimurium* by Oral Immunization of Chickens with Avirulent Δ cya , Δ crp *S. Typhimurium, Res. Microbiol.* 141:839–850 (1990).
Heuzenroeder et al., Molecular cloning and expression in *Escherichia coli* K–12 of the 0101 rfb region from *E. coli* B41 (0101:K99/F41) and the genetic relationship to other 0101 rfb loci, *Mol. Microbiol.* 3:295–302 (1989).
Hone et al., A chromosomal integration system for stabilization of heterologous genes in *Samonella* based vaccine strains, *Microb. Pathog.* 5:407–418 (1988).
Nakayama et al., Construction of an ASD+ Expression–Cloning Vector: Stable Maintenance and High Level Expression of Cloned Genes in a *Salmonella* Vaccine Strain, *Bio/Technology* 6:693–694 (1995).
Neal et al., Molecular cloning and expression in *Escherichia coli* K–12 of chromosomal genes determining the O antigen of an *E. coli* 02:K1 strain, *FEMS Microbiol. Lett.* 82:345–352 (1991).
Pier et al., Clearance of *Pseudomonas aeruginosa* from the Murine Gastrointestinal Tract Is Effectively Mediated by O–Antigen–Specific Circulating Antibodies, *Infect. Immun.* 63:2818–2825 (1995).
Porter et al., Virulence of *Salmonella typhimurium* Mutants for White Leghorn Chicks, *Avian Dis.* 37:265–273 (1993).
Strugnell et al., Stable expression of foreign antigens from the chromosome of *Salmonella typhimurium.* vaccine strains, *Gene* 88:57–63 (1990).
Sugiyama et al., Expression of the Cloned *Escherichia coli* 09 rfb Gene in Various Mutant Strains of *Salmonella typhimurium, J. Bacteriol.* 173:55–58 (1991).
Valvano et al., Molecular Cloning and Expression in *Escherichia coli* K–12 of Chromosal Genes Determining the 07 Lipopolysaccharide Antigen of a Human Invasive Strain of *E. coli* 07:K1, *Infect. Immun.* 57:937–943 (1989).

* cited by examiner

Primary Examiner—Robert A. Schwartzman
Assistant Examiner—Anne Marie S. Beckerleg
(74) Attorney, Agent, or Firm—Howell & Haferkamp (57) ABSTRACT

A vaccine for protecting birds against infection by avian pathogenic gram negative microbes is disclosed. The vaccine is a recombinant Salmonella strain expressing O-antigen of an avian pathogenic gram negative microbe such as an *E. coli* strain that is pathogenic in poultry. The recombinant Salmonella strain also does not express Salmonella O-antigen. Methods of using the vaccine to immunize birds are also disclosed.

30 Claims, 5 Drawing Sheets

LIVE ATTENUATED SALMONELLA VACCINES TO CONTROL AVIAN PATHOGENS

BACKGROUND OF THE INVENTION

This invention relates generally to vaccines for poultry and other birds and, more particularly, to vaccines for protecting poultry and other birds against infection by avian pathogenic gram-negative bacteria.

DESCRIPTION OF THE RELATED ART

Avian pathogenic *E. coli* (APEC) strains cause a number of related diseases in poultry and other birds, including air sacculitis, cellulitis, colibacillosis, coligranuloma, colisepticemia, Hjarre's disease, omphalitis, peritonitis, salpingitis, synovitis (Gross, W. B. in *Diseases of Poultry*, Calnek et al., eds., Iowa State University Press, p. 138–144, 1991; Messier et al., *Avian Diseases* 37:839–844, 1993). These diseases and other diseases caused by gram-negative avian pathogens can lead to increased rates of feed conversion carcass condemnation, or death of the animal, resulting in millions of dollars lost to the poultry industry each year. Norton, R. A. *Broiler Industry*, February 1998, pp. 28–32.

Contamination of poultry products by Salmonella is a significant source of Salmonella infection in humans, which causes gastroenteritis, and thus is a major public health concern. Oral administration of live cells from *S. typhimurium* strains having attenuating deletions in the cya and crp genes has been shown to provide excellent protection against wild-type Salmonella challenge in chickens (Hassan et al., *Res. Microbiol.* 141:839–850, 1990; Hassan et al., *Infect. Immun.* 62:5519–5527, 1994) and systems for stable expression of heterologous antigens in such strains have been developed (Hone et al., *Microb. Pathog.* 5:407–418, 1988; Strugnell, et al., Gene 88:57–63, 1990; Galan et al., Gene 94:29–35; 1990; Nakayama et al., *Bio/Technology* 6:693–697, 1995).

APEC strains are represented primarily by only a few serotypes, O1, O2, O35 and O78 (Cloud et al., *Avian Dis.* 29:1084–1093, 1985, Glantz et al., *Avian Dis.* 6:322–328, 1962; Gross, supra), while Salmonella serotypes most prevalent in poultry are in the B, C and D groups. O-serotypes of gram-negative bacteria such as *E. coli* and Salmonella are determined at the molecular level by the so-called O-antigen structure, also termed O-specific chain or O-polysaccharide (O-PS), which generally is comprised of varying lengths of polymerized identical sugar units anchored in the bacterial outer membrane as the outermost component of lipopolysaccharide (LPS) molecules (Helander et al., in *Molecular Biology and Biotechnology: A Comprehensive Desk Reference*, R. A. Meyers, ed., VCH Publishers, Inc., 1995).

Specific antibody against LPS O-antigen has been shown to be protective in mammalian models of extraintestinal *E. coli* infections in humans (Cryz et al., *Vaccine* 13;449–453, 1995; Pluschke et al., *Infect. Immun.* 49:365–370, 1985) and LPS O-antigen has been recognized as a protective antigen for other gram negative pathogens (Ding et al., *J. Med. Microb.* 31:95–102, 1990; Michetti et al., *Infect. Immun.* 60:1786–1792, 1992; Robbins et al., *Clin. Infect Dis.* 15:346–361, 1992). In addition, several research groups have reported using attenuated Salmonella and Salmonella-*E. coli* hybrids as vaccine delivery vehicles for O-antigens of several human pathogens, including *Shigella sonnei, Vibrio cholerae*, and *Pseudomonas aeruginosa.* (13lack et al., *J. Infect. Dis.* 155:1260–1265, 1987; Formal et al., *Infect. Immun.* 34:746–750, 1981; Pier et al., *Infect. Immun.* 63:2818–2825, 1995); (Morona et al., U.S. Pat. No. 5,110,588). However, until the work described herein, immunization of poultry with live, attenuated Salmonella expressing an APEC O-antigen had not been reported.

LPS O-antigen made by *E. coli* and Salmonella bacteria is comprised of lipid A, an R-core oligosaccharide, and the O-specific polysaccharide (O-PS), which are covalently linked in that order. Sugiyama et al., *J. Bacteriol.* 173:55–58, 1991. In *S. typhimurium*, synthesis of the R-core moiety is directed by the rfa locus and certain housekeeping genes such as galE, galU, and pgi, while O-PS synthesis is directed by the rfb gene cluster, which encodes enzymes involved in biosynthesis of the monomer sugar unit, and the rfc gene, which encodes the O-antigen polymerase responsible for the polymerization of the sugar unit into a high molecular weight polysaccharide chain. Sugiyama et al., supra.

One group investigating the genes required for synthesis of LPS O-antigen in *E. coli* O9 introduced a plasmid containing the rfb locus from *E. coli* O9 into *S. typhimurium* wild-type and mutant strains with defects in the rfb, rfc, or rfe loci and reported that the wild-type strain containing the plasmid expressed LPS specific for both *E. coli* O9 and *S. typhimurium* on the cell surface, while the rfc mutant was expressed only O9-specific LPS. *E. coli* O-antigen was also synthesized in the *S. typhimurium* rfb mutant but not in the rfe mutant. Sugiyama et al., supra. This group concluded that gene products of the *S. typhimurium* rfa and *E. coli* O9 rfb loci can cooperate to synthesize *E. coli* O9-antigen on the R-core of *S. typhimurium.* However, this group did not report whether any of these recombinant *S. typhimurium* constructs could grow within an animal host or generate a protective host immune response against wild-type *E. coli* O9 or *S. typhimurium*. Accordingly, a need exists for a bivalent vaccine to control Salmonella and *E. coli* infection in poultry. Such a vaccine would simultaneously benefit the public health and reduce the costs of poultry production.

SUMMARY OF THE INVENTION

In one embodiment the present invention is directed to a vaccine that protects birds against infection by an avian pathogenic gram-negative ($AP_{G-N}$) microbe. The vaccine comprises live cells of a recombinant Salmonella strain expressing O-antigen of the $AP_{G-N}$ microbe due to integration into the Salmonella chromosome of the rfb gene cluster and the rfc gene of the $AP_{G-N}$ (hereinafter used interchangeably with $AP_{G-N}$ rfb/rfc gene cluster). The recombinant Salmonella strain, which is an attenuated mutant of a virulent Salmonella strain, does not express O-antigen of the virulent Salmonella strain due to a mutation in the Salmonella rfb gene cluster and/or in the Salmonella rfc gene. In a preferred embodiment, the $AP_{G-N}$ microbe is an APEC strain and the $AP_{G-N}$ rfb/rfc gene cluster is an APEC rfb/rfc gene cluster.

This recombinant Salmonella strain has other features that make it particularly useful as a vaccine in poultry and other birds. First, the vaccine can be formulated for oral administration and oral vaccines are known to stimulate the gut associated lymphoid tissue (GALT), including mucosal, humoral and cellular immune responses. Oral, live vaccines also cost less to produce and are easier to administer in the field than injectable vaccines. Second, the lack of expression of LPS O-antigen specific for the carrier strain avoids any interference that the carrier LPS O-antigen might have on expression of the $AP_{G-N}$ O-antigen or its recognition by the vaccine recipient's immune system. Third, the recombinant Salmonella strain can protect against both $AP_{G-N}$ microbes and the parental Salmonella strain because it expresses other cell-surface antigens of the parental Salmonella strain. In addition, for vaccines expressing O-antigen from an APEC strain, use of Salmonella rather than *E. coli* as the carrier bacteria should provide a more vigorous immune response against the APEC O-antigen because while *S. enterica* subspecies persist in the spleen and bursa of Fabricius, *E. coli* does not effectively invade these lymphoid tissues or is quickly killed even if occasionally successful in entering them.

In some embodiments, the recombinant Salmonella strain used in the vaccine also contains a recombinant polynucleotide encoding a desired gene product. A preferred gene product is an antigen from an avian pathogenic gram-positive ($AP_{G-P}$) microbe or from a eukaryotic avian pathogen.

In another embodiment, the invention provides a multivalent vaccine for immunizing birds against at least two avian pathogenic gram-negative ($AP_{G-N}$) microbes which comprises live cells of a recombinant Salmonella strain expressing an O-antigen of each of the $AP_{G-N}$ microbes, the recombinant Salmonella strain having an rfb/rfc gene cluster of each of the $AP_{G-N}$ microbes integrated into the Salmonella chromosome and having a mutation in the Salmonella rfb gene cluster or in the Salmonella rfc gene which inactivates expression of Salmonella O-antigen, wherein the recombinant Salmonella strain is an attenuated mutant of a virulent Salmonella strain. In a preferred embodiment, one or both of the $AP_{G-N}$ microbes is an APEC strain.

In yet another embodiment, the invention provides a multivalent vaccine for immunizing a bird against at least two $AP_{G-N}$ microbes which comprises a mixture of live cells of first and second recombinant Salmonella strains, the first recombinant Salmonella strain having an rfb/rfc gene cluster of a first $AP_{G-N}$ microbe integrated into the Salmonella chromosome and expressing O-antigen of the first $AP_{G-N}$ microbe and the second recombinant Salmonella strain having an rfb/rfc gene cluster of a second $AP_{G-N}$ microbe integrated into the Salmonella chromosome and expressing O-antigen of the second $AP_{G-N}$ microbe, wherein each of the first and second recombinant Salmonella strains has a mutation in the Salmonella rfb gene cluster or in the Salmonella rfc gene which inactivates expression of Salmonella O-antigen, and wherein each of the first and second recombinant Salmonella strains is an attenuated mutant of a virulent Salmonella strain. In a preferred embodiment, one or both of the recombinant Salmonella strains in the multivalent vaccine express O-antigen of an APEC strain.

The present invention in other embodiments is directed to methods for immunizing birds against infection by $AP_{G-N}$ microbes. These methods include a method for immunizing a bird against an $AP_{G-N}$ microbe which comprises administering to the bird an immunologically effective amount of a vaccine comprising live cells of a recombinant Salmonella strain expressing O-antigen of the $AP_{G-N}$ microbe, the recombinant Salmonella strain having an rfb/rfc gene cluster of the $AP_{G-N}$ microbe stably integrated into the Salmonella chromosome and having a mutation in the Salmonella rfb gene cluster or in the Salmonella rfc gene which inactivates expression of Salmonella O-antigen, wherein the recombinant Salmonella strain is an attenuated mutant of a virulent Salmonella strain. The methods also include a method for simultaneously immunizing a bird against more than one $AP_{G-N}$ microbes which comprises administering to the bird an immunologically effective amount of a multivalent vaccine as described above. Also included is a method for simultaneously immunizing a bird against an $AP_{G-N}$ microbe and the carrier Salmonella species which comprises administering to the bird an immunologically effective amount of any of the vaccines as described above.

In still another embodiment, the invention provides a method of making a vaccine for immunizing a bird against an $AP_{G-N}$ microbe strain. The method comprises the steps of selecting a Salmonella strain capable of colonizing the bird, integrating into the Salmonella chromosome an rjb/rfc gene cluster from the $AP_{G-N}$ microbe, introducing a mutation into the Salmonella rfb gene cluster and/or into the Salmonella rfc gene, and isolating recombinant Salmonella bacteria which express O-antigen characteristic of the $AP_{G-N}$ microbe but which do not express Salmonella O-antigen. In one embodiment the selected Salmonella strain is an attenuated mutant of a virulent Salmonella strain. In another embodiment, the selected Salmonella strain is a virulent Salmonella strain and the method further comprises the step of introducing into the virulent Salmonella strain an attenuating mutation into a Salmonella virulence gene and isolating mutants having attenuated virulence as compared to the virulent Salmonella strain.

Among the several advantages achieved by the present invention, therefore, is the provision of live, recombinant Salmonella vaccines capable of protecting birds and particularly poultry against infection by APEC strains and other $AP_{G-N}$ microbes, and methods for making such vaccines, the provision of multivalent vaccines useful for simultaneously protecting birds against infection by two or more $AP_{G-N}$ microbes, the provision of methods for immunizing birds against APEC strains and other $AP_{G-N}$ microbes, and the provision of a method for immunizing birds against both APEC and Salmonella bacteria.

BRIEF DESCRIPTION OF THE DRAWINGS

FIGS. 2(A & B) shows digitized images of western blots of LPS isolated from the indicated bacteria strain probed with (FIG. 2A) anti-*S. typhimurium* group B LPS antibody or (FIG. 2B) anti-O78 LPS antibody;

FIGS. 3(A & B) shows digitized images of western blots of LPS isolated from the indicated bacteria strain probed with (FIG. 3A) anti-*S. typhimurium* group B LPS antibody or (FIG. 3B) anti-O 78 LPS antibody, with a molecular weight marker included in the gel for the blot shown in FIG. 3A;

DETAILED DESCRIPTION OF THE INVENTION

The present invention is based on the discovery that *Salmonella enterica* subspecies, in particular *S. typhimurium*, can be engineered to express O antigen of $AP_{G-N}$ microbes, in particular of O78 and O1 APEC strains, in an immunogenic form on the cell surface without such expression interfering with in vivo growth or colonization of the poultry GALT by the Salmonella carrier. In addition, the inventor herein has discovered that oral administration of such recombinant Salmonella strains to chickens results in a significant reduction in the ability of virulent APEC strains to infect and cause disease in the vaccinated chickens.

Thus, one embodiment of the invention is a vaccine for immunization of birds against an avian pathogenic gram-negative microbe ($AP_{G-N}$) comprising live cells of a recombinant Salmonella strain expressing O-antigen of the $AP_{G-N}$ strain. The $AP_{G-N}$ O-antigen is expressed in an immunogenic form, meaning that the $AP_{G-N}$ O-antigen moiety is part of a complete LPS O-antigen molecule in which the $AP_{G-N}$ O-antigen is attached to an LPS core moiety and, upon administration to a bird, is capable of generating antibodies that react with LPS O-antigen of the wild-type $AP_{G-N}$ microbe. Typically, the LPS core moiety is synthesized by the recombinant Salmonella carrier, but in some embodiments the LPS core may be from the same $AP_{G-N}$ microbe as the O-antigen or from a different $AP_{G-N}$ microbe.

It is contemplated that the vaccine can be used to immunize all types of birds, including chickens, turkeys, ducks, geese, pheasants and other domesticated birds categorized as poultry, as well as non-domesticated birds such as wild turkeys and exotic species such as parrots, parakeets, etc., against any $AP_{G-N}$ microbe now known or subsequently determined to be pathogenic in birds. Such $AP_{G-N}$ microbes include but are not limited to: (1) APEC strains such as *E. coli* serotypes O1, O2, O3, O6, O8, O15, O18, O35, O71, O74, O78, O87, O88, O95, O103 and O109; (2) avian pathogenic Salmonella strains, e.g., group C and group D strains; and (3) species of the following genera: Campylobacter, Bacteroides, Bordetella, Haemophilus, Pasteurella, Francisella, Actinobacillus, Klebisella, Moraxella, Pseudomonas, Proteus, and Ornithobacterium. Preferably, the recombinant Salmonella strain expresses O-antigen of an APEC strain. More preferably, the APEC O-antigen is characteristic of the O1, O2, O35 or O78 serotypes and most preferably the O-antigen is O1 LPS, O2 LPS or O78 LPS.

The recombinant Salmonella strain used in the vaccine is prepared by integrating the rfb/rfc gene cluster from a desired $AP_{G-N}$ microbe into the chromosome of a suitable Salmonella strain. Salmonella strains for use as the carrier bacteria may be derived from any Salmonella species that is capable of colonizing birds, preferably poultry. Such species include but are not limited to *S. typhimurium, S. enteriditis, S. gallinarum, S. pullorum, S. arizona, S. heidelberg, S. anatum, S. hadar, S. agana, S. montevideo, S. kentucky, S. infantis, S. schwarzengrund, S. saintpaul, S. brandenburg, S. instanbul, S. cubana, S. bredeney, S. braenderup, S. livingstone, S. berta, S. california, S. senfenberg*, and *S. mbandaka*. As used herein, "colonizing" means the Salmonella species is able to attach to, invade and persist in one or more of the following tissues in the vaccinated bird: lung, spleen, liver, bursa of Fabricius, and ceca. Preferably, the recombinant Salmonella strain is derived from *S. typhimurium, S. gallinarum, S. pullorum*, or *S. enteriditis*. Most preferably, the $AP_{G-N}$ rfb/rfc gene cluster is inserted into a strain of *S. typhimurium.*

As used herein, an $AP_{G-N}$ rfb/rfc gene cluster contains all the genes necessary for synthesis of O-antigen characteristic of that $AP_{G-N}$ microbe, including all rfb genes whose products are required for biosynthesis of the monomer sugar unit, as well as the rfc gene, which encodes the O-antigen polymerase needed for polymerization of the sugar units. The terms rfb genes and ifc gene are intended to mean those genes of any $AP_{G-N}$ microbe identified as encoding gene products having the same function in O-antigen biosynthesis as the products of an *E. coli* rjb/rfc gene cluster. In most *E. coli* and Salmonella serotypes, the rfc gene is tightly linked to the rfb gene cluster, which in *E. coli* is about 10 kb in length and located near 45 minutes on the *E. coli* genetic map. However, in some *E. coli* strains, as in *S. typhimurium*, the rfc gene is not linked to the rfb gene cluster and can be found a significant distance away. For example, in *S. typhimurium*, the rfb gene cluster, which is about 21 kb, extends from 44.9–45.3 centisomes on the genetic map of *S. typhimurium* while the rfc gene is located at 35.7 centisomes.

A functionally complete $AP_{G-N}$ rfb/rfc gene cluster can readily be cloned using routine cosmid cloning methodology, as previously described for cloning bacteria rfb/rfc gene clusters. See, for example, Viret et al., EP 0 564 689 B1; Neal et al., *FEMS Microbiol. Lett.* 82:345–352, 1991; Haraguchi et al., *Microb. Pathog.* 6:123–132, 1989; *Microb. Pathog.* 10:351–361, 1991; Heuzenroeder et al., *Mol. Microbiol.* 3:295–302, 1989; Bastin et al., *Mol. Microbiol.* 5:2223–2231, 1991; and Valvano et al., *Infect. Immun.* 57:937–943, 1989. General cosmid cloning techniques are also described in detail in Sambrook et al., *Molecular Cloning: A Laboratory Manual,* 2nd Ed., Cold Spring Harbor Laboratory Press, 1989. In brief, a cosmid library of chromosomal DNA from the desired $AP_{G-N}$ microbe is prepared in the *E. coli* K-12 strain, which does not produce O-antigen due to mutations in the rfb region. The cosmid library is plated and isolated colonies are screened for expression of the $AP_{G-N}$ O-antigen using antisera specific for the O-antigen of the desired $AP_{G-N}$ strain. The $AP_{G-N}$ chromosomal DNA fragment can be isolated from positive cosmid clones and further characterized using standard techniques, such as restriction mapping and subcloning, to determine the minimal amount of $AP_{G-N}$ DNA required to direct synthesis of $AP_{G-N}$ O-antigen. This minimal amount is herein referred to as the rfb/rfc gene cluster. For those $AP_{G-N}$ microbes where the rfc gene is located a considerable distance from the rfb gene cluster, a single $AP_{G-N}$ chromosomal fragment containing a functional rfb/rfc gene cluster may not be represented in the cosmid library. In such cases, additional routine cloning and screening experiments may need to be performed to clone the rfc gene and construct a recombinant fragment containing both the rfb genes and the rfc gene. The rfb/rfc gene cluster is then transfected as a cosmid or plasmid into the selected Salmonella strain and the LPS produced by the resulting recombinant is analyzed by methods known in the art and those briefly described below.

It has been reported that the Salmonella LPS core moiety can not accept heterologous O-antigen of some bacteria, resulting in unbound O-antigen, which is probably less immunogenic than complete LPS molecules carrying the heterologous O-antigen covalently attached to the core moiety of the carrier bacteria (EP 0 564 689 B1; Morona et al., U.S. Pat. No. 5,110,588). Recombinant strains expressing complete LPS O-antigen can be distinguished from those expressing unbound O-antigen by SDS-PAGE analysis of LPS extracted from late exponential or stationary cultures using a rapid small-scale mini-prep method (Hitchcock and Brown, *J. Bacteriol.* 154:269–277, 1983). The separated LPS molecules can be detected in the gel by silver staining or by immunoblot analysis using an antibody specific for the O-antigen. Complete LPS O-antigen (also referred to herein as smooth, or S-type LPS) will produce a ladder of high molecular weight bands detectable by either silver staining or immunoblot analysis, whereas unbound O-antigen does not produce a ladder and will be detected as a smear by silver staining or probing with antibody. In such cases, the Salmonella rfa locus, which directs synthesis of the LPS core, can be swapped with an rfa locus of another bacteria, such as *E. coli* K-12 or the $AP_{G-N}$ microbe, to derive a combination of rfa and $AP_{G-N}$ rfb/rfc gene clusters that will direct synthesis of $AP_{G-N}$ O-antigen in an immunogenic form.

To assure stable expression of the heterologous antigen and eliminate the need for use of antibiotics to maintain an extrachromosomal element in the Salmonella strain, the $AP_{G-N}$ rfb/rfc gene cluster is integrated into the Salmonella chromosome. This can be accomplished by any known methodology, preferably by a defined deletion/insertion mutation into a virulence gene to produce an attenuated mutant as described below. Alternatively, $AP_{G-N}$ rfb/rfc gene cluster can be integrated in a manner that does not attenuate the recombinant Salmonella strains.

The recombinant Salmonella strain also contains a mutation in the Salmonella rfc gene which inactivates expression of the Salmonella O-antigen polymerase. Salmonella mutants defective in the O-antigen polymerase produce LPS molecules termed semirough (SR LPS), which have at most one O-antigenic sugar unit attached to any given core unit instead of the usual 30–40 sugar units seen in $Rfc^+$ strains. These SR LPS molecules are less likely to interfere with the ability of the much longer APEC LPS O-antigen to stimulate a protective immune response. The recombinant Salmonella strain can be prepared from a strain already containing an rfc mutation or the rfc mutation can be introduced at the same time as, or after, integration of the APEC rfb/rfc gene clusters into the Salmonella chromosome.

Salmonella rfc mutants can be created using routine techniques known in the art. For example, random transposon insertions can be made in the chromosome of the desired Salmonella strain (see, e.g., Curtiss, U.S. Pat. No. 5,672,345) and mutants having a Rfc phenotype (i.e., expression of SR LPS) isolated (Collins et al., *J. Bacteriol.*:173:2521–2529, 1991). Alternatively, a deletion mutation can be introduced into the Salmonella rfc gene using recombinant DNA techniques such as those described in the Examples herein. In brief, the rfc gene of *S. typhimurium* has been cloned and sequenced and is believed to be conserved among Salmonella strains of serogroups A, B and D1 (Collins et al., supra). Based on this information the ifc gene from a Salmonella strain belonging to one of these serogroups can be cloned and used to construct a suicide plasmid containing a deletion in the cloned rfc gene. Introduction of this plasmid into an $rfc^+$ Salmonella strain will lead to homologous recombination between the chromosomal rfc gene and the Δrfc plasmid. The transformed cells are then cultured on media lacking selection for the plasmid and the isolates screened for the Rfc phenotype.

Salmonella mutants can be tested for an Rfc phenotype by SDS-PAGE analysis of LPS isolated from the bacteria and detection of a high proportion of SR LPS with an O-sugar unit specific for the Salmonella strain. Another procedure that can be used to screen Salmonella mutants for the Rfc phenotype is by a bacteriophage sensitivity assay, using a phage specific for s-type LPS. For example, *S. typhimurium* and other Salmonella group B strains having an $Rfc^+$ phenotype (i.e., express s-type LPS) are lysed by P22 whereas Rfc mutants of these strains are resistant to P22-mediated lysis as P22 does not recognize the SR LPS expressed by these mutant strains.

It is also contemplated that a recombinant Salmonella strain expressing $AP_{G-N}$ O-antigen from more than one $AP_{G-N}$ microbe can be constructed using techniques similar to those described herein for preparing strains expressing a single $AP_{G-N}$ O-antigen.

Because the vaccine comprises live cells of the recombinant Salmonella strain, it is possible that live, recombinant Salmonella bacteria could be transmitted to human consumers of poultry food products such as eggs and meat. In addition, *S. enterica* species can cause disease in very young birds. Thus, an important feature of the invention is that the recombinant Salmonella strain is an attenuated mutant of a virulent strain of an *S. enterica* species. As used herein, an attenuated mutant means that the recombinant Salmonella strain has the ability to colonize and replicate in a vaccinated bird but which is substantially incapable of causing the disease symptoms associated with infection of the particular avian species being treated or infection of humans by its virulent counterpart. By the term "substantially incapable of causing disease symptoms" is meant the attenuated mutant either produces no disease symptoms or produces less severe and/or a fewer number of such symptoms. However, an attenuated mutant strain is not necessarily incapable of causing some effect on normal physiological function in the vaccine recipient or a human and may be a pathogen in avian species other than the intended vaccine recipient as well as in other nonhuman hosts.

The recombinant Salmonella strain can be derived from naturally occurring avirulent mutants of virulent strains of *S. enterica* species, or by introducing attenuating mutations into wild-type, virulent strains using well-known techniques. Attenuating mutations can be in biosynthetic genes, regulatory genes and/or genes involved in virulence. (See Doggett and Brown, in *Mucosal Vaccines*, Kiyono et al., eds., Academic Press, San Diego, 1996, pp. 105–118). Examples of genes whose mutation will lead to attenuation include, but are not limited to a mutation in a pab gene, a pur gene, an aro gene, asd, a dap gene, nadA, pncB, galE, pmi, fur, rpsL, ompR, htrA, hemA, cdt, cya, crp, phoP, phoQ, rfc, poxA, galU and combinations thereof. Mutations can be insertions, partial or complete deletions or the like so long as expression of the gene is diminished and virulence is decreased. The skilled artisan will readily appreciate that any suitable gene mutation can be used in the present invention so long as the mutation of that gene renders the microorganism attenuated. Preferably, the carrier microbes of the invention have at least two mutations, each of which act to attenuate the microbe and which, in combination, significantly increase the probability that the microbe will not revert to wild-type virulence.

Methods are known in the art that can be used to generate mutations to produce the attenuated recombinant Salmonella strain of the present invention. For example, the transposon, Tn10, can be used to produce chromosomal deletions in a wide variety of bacteria, including Salmonella (Kleckner et al., *J. Mol. Biol.* 116:125–159, 1977; EPO Pub. No. 315,682; U.S. Pat. No. 5,387,744).

Recently, new methods have become available for producing specific deletions in genes. These methods involve initially selecting a gene in which the deletion is to be generated. In one approach the gene can be selected from a genomic library obtained commercially or constructed using methods well known in the art (Sambrook et al., Molecular Cloning: A Laboratory Manual, 2nd Ed., 1989, Cold Spring Harbor Press, Cold Spring Harbor, N.Y.). Clones containing the gene are isolated from the genomic library by complementation of a strain which contains a mutation in the same gene. Alternatively, when the DNA sequence of the gene is known, selected primers for the polymerase chain reaction method (PCR) can amplify the gene, often with some flanking sequence, from a sample of bacteria or from purified genomic DNA and the PCR product can be inserted into a cloning vector.

A specific deletion in the selected gene can be generated by either of two general methods. The first method generates a mutation in a gene isolated from a population of clones contained in a genomic DNA library using restriction enzymes and the second method generates the mutation in a gene of known sequence using PCR. Using the first method, the position of the gene on a vector is identified using transposon tagging and a restriction map of the recombinant DNA in the vector is generated. Information derived from the transposon tagging allows all or a portion of a gene to be excised from the vector using the known restriction enzyme sites. The second method, which is based upon PCR methodology, can be used when the DNA sequence of the gene is known. According to this method, divergent PCR primers amplify the upstream and downstream regions flanking a specified segment of DNA to be deleted from the gene and generate a PCR product consisting of the cloning vector and upstream and downstream flanking nucleotide sequences (Innes et al. Eds., PCR Protocols, 1990, Academic Press, New York). In a variation of this method, PCR products are produced representing portions of the gene or flanking sequence, which are then joined together in a cloning vector.

The DNA containing the mutant gene can be introduced into the bacterial host by transformation using chemical means or electroporation, by recombinant phage infection, or by conjugation. In preferred embodiments, the mutant gene is introduced into the chromosomes of the bacteria which can be accomplished using any of a number of methods well known in the art such as, for example, methods using temperature-sensitive replicons (Hamilton et al., J. Bacteriol. 171:4617–4622, 1989), linear transformation of recBC mutants (Jasin et al., J. Bacteriol. 159:783–786, 1984), or host restricted replicons known as suicide vectors (Miller et al., J. Bacteriol. 170:2575–2583, 1988). The particular method used is coupled with an appropriate counter selection method such as, for example, fusaric acid resistance or sucrose resistance followed by subsequent screening for clones containing the mutant allele based upon phenotypic characteristics or by using PCR, nucleic acid hybridization, or an immunological method.

The recombinant Salmonella strain used in the present invention can also be used to deliver a desired gene product to the vaccinated bird. The term "gene product" as used herein refers to any biological product or products produced as a result of the biochemical reactions that occur under the control of a gene. The gene product can be, for example, an RNA molecule, a peptide, a protein, or a product produced under the control of an enzyme or other molecule that is the initial product of the gene, i.e., a metabolic product. For example, a gene can first control the synthesis of an RNA molecule which is translated by the action of ribosomes into an enzyme which controls the formation of glycans in the environment external to the original cell in which the gene was found. The RNA molecule, the enzyme, and the glycan are all gene products as the term is used here. Examples of desired gene products include but are not limited to antigens, various host cell proteins, pharmacologically active products, toxins, and apoptosis-modulating agents.

An antigen or immunogen is intended to mean a molecule containing one or more epitopes that can stimulate a host immune system to make a secretory, humoral and/or cellular immune response specific to that antigen. An epitope can be a site on an antigen to which an antibody specific to that site binds. For protein antigens, an epitope could comprise 3 amino acids in a spatial conformation which is unique to the epitope; generally, an epitope will consist of at least 6 consecutive amino acids, or more usually, at least 10–12 consecutive amino acids of the antigen. The term "epitope" is intended to be interchangeable with the term "antigenic determinant" as used herein. The term "epitope" is also intended to include T-helper cell epitopes in which an antigenic determinant is recognized by T-helper cells through association with major histocompatibility complex class II molecules. In addition, the term epitope includes any antigen, epitope or antigenic determinant which is recognized by cytotoxic T cells when presented by a MHC class I molecule on the surface of an antigen presenting cell. A cytotoxic T cell epitope can comprise an amino acid sequence of between about 6 to about 11 consecutive amino acids, and preferably comprises a sequence of 8 or 9 consecutive amino acids.

If the desired gene product is an antigen from a bacterial, fungal, parasitic or viral disease agent, the recombinant Salmonella strain can be used to vaccinate birds against diseases caused by such agents at the same time as vaccinating against an $AP_{G-N}$ microbe. For example, the recombinant Salmonella strain could be used to deliver an antigen from an avian pathogenic microbe that does not express O-antigen such as gram-positive ($AP_{G-P}$) bacteria. Such microbes include but are not limited to species of Mycoplasma, Listeria, Borrelia, Chlamydia, Clostridia, Corynebacteria, Coxiella, Eysipelothrix, Flavobacteria, Staphylococcus, and Streptococcus. Examples of fungal and parasitic avian pathogens known to infect poultry are species of Amoebotaenia, Aproctella, Ascaridia, Aspergillus, Candida, Capillaria, Cryptosporidium, Cyathostroma, Dispharynx, Eimeria, Fimbriaria, Gongylonemia, Heterakis, Histomonas, Oxyspirura, Plasmondium, Raillietina, Strongyloides, Subulura, Syngamus, Tetrameres, and Trichostrongylus. Viruses known to infect poultry include adenoviruses (e.g., hemorrhagic enteritis virus), astroviruses, coronaviruses (e.g., Infectious bronchitis virus), paramyxoviruses (e.g., Newcastle disease virus), picornaviruses (e.g., avian encephalomyelitis virus), pox viruses, retroviruses (e.g., avian leukosis/sarcoma viruses), reoviruses, and rotaviruses. Preferred gene products for use as antigens are polysaccharides and proteins, including glycoproteins and lipoproteins. Antigen-encoding genes from these prokaryotic and eukaryotic organisms can be cloned and expressed in the recombinant Salmonella strain using standard techniques.

In other embodiments, the desired gene product directs the expression of a gamete-specific antigen which is capable of eliciting an immune response that confers an antifertility effect upon the immunized animal (See, U.S. Pat. No. 5,656,488).

As used herein, vaccine means an agent used to stimulate the immune system of an animal so that protection is provided against an antigen not recognized as a self-antigen by the immune system. Immunization refers to the process of inducing a continuing high level of antibody and/or cellular immune response in which T-lymphocytes can either kill the pathogen and/or activate other cells (e.g., phagocytes) to do so in the immunized animal, which is directed against a pathogen or antigen to which the animal has been previously exposed. In this application the phrase "immune system" is intended to refer to the anatomical features and mechanisms by which an avian species produces antibodies against an antigenic material which invades the cells of the vertebrate or the extra-cellular fluid of the individual and is also intended to include cellular immune responses.

In the case of antibody production, the antibody so produced can belong to any of the immunological classes, such as immunoglobulins, A, D, E, G or M. Of particular interest are vaccines which stimulate production of immunoglobulin A (IgA) since this is the principle immunoglobulin produced by the secretory system of avian species, although vaccines of the invention are not limited to those which stimulate IgA production. For example, vaccines of the nature described herein are likely to produce a broad range of other immune responses in addition to IgA formation, for example cellular and humoral immunity. Immune responses to antigens are well studied and widely reported.

The avirulent microbes of this invention can also be used as vectors for synthesis of other proteins, including immunoregulatory molecules made by avian species and pharmacologically active products that might stimulate or suppress various physiological functions (i.e., growth rate, fat or protein content, etc.).

The desired gene product is encoded by a recombinant polynucleotide. The term "recombinant polynucleotide" is defined herein to refer to the result of laboratory manipulations which results in the introduction into the Salmonella strain of a promoter operably linked to a gene from various endogenous and/or exogenous sources. The promoter is one that is functional in the Salmonella strain to produce expression of the gene. The gene can be of chromosomal, plasmid, or viral origin. A gene as used herein is any biological unit of heredity capable of producing a desired gene product. It is not, however, necessary that the gene be a complete gene as is present in the parent organism and capable of producing or regulating the production of a macromolecule such as for example, a functioning polypeptide. The recombinant polynucleotide may, thus, encode all or part of an antigenic product. A gene can also refer to a polynucleotide having a sequence mutated from the naturally-occurring sequence found in the parent organism. The recombinant polynucleotide can also refer to a long section of DNA coding for several gene products, one or all of which can be antigenic or part of a biosynthetic pathway that leads to the desired gene product. For example, such a long section of DNA could encode 5 to 15 proteins necessary for the synthesis of fimbrial antigens (fimbriae), which mediate adhesion of pathogens to host cells (Bäumler et al., supra). The induction of an immune response against fimbriae can provide protection against the pathogen. It is to be understood that the term gene as used herein further includes DNA molecules lacking introns such as, for example, is the case for cDNA molecules, so long as the DNA sequence encodes the desired gene product. The recombinant polynucleotide encoding the desired gene product may include DNA sequences other than the promoter such as termination sequences and other regulators of prokaryotic gene expression.

The recombinant polynucleotide encoding a desired gene product can be transferred into the Salmonella strain in the form of a plasmid, phage or cosmid vector by various means such as conjugation, electroporation, or transformation (uptake of naked DNA from the external environment, which can be artificially induced by the presence of various chemical agents, such as calcium ions). Other methods such as transduction are also suitable, wherein the recombinant DNA in the form of a transducing phage or cosmid vector is packaged within a phage. Once the recombinant polynucleotide is in the carrier Salmonella, it may continue to exist as a separate autonomous replicon or it may insert into the Salmonella chromosome and be reproduced along with the chromosome during cell division.

Preferably, the recombinant polynucleotide is incorporated into a "balanced-lethal" system which selects for microorganisms containing and capable of expressing the desired gene product by linking the survival of the microorganism to the continued presence of the recombinant polynucleotide. "Balanced-lethal" mutants of this type are characterized by a lack of a functioning native chromosomal gene encoding an enzyme which is essential for cell survival, preferably an enzyme which catalyzes a step in the biosynthesis of diaminopimelic acid (DAP) and even more preferably a gene encoding beta aspartate semialdehyde dehydrogenase (Asd). DAP pathway enzymes and Asd are required for cell wall synthesis. "Balanced-lethal" mutants also contain a recombinant gene which can serve to complement the non-functioning chromosomal gene and this complementing recombinant gene is structurally linked to the recombinant polynucleotide encoding the desired gene product. Loss of the complementing recombinant gene causes the cells to die by lysis when the cells are in an environment where DAP is lacking. This strategy is especially useful since DAP is not synthesized by eukaryotes and, therefore, is not present in infected avian tissues. Methods of preparing these types of "balanced lethal" microbes are disclosed in U.S. Pat. No. 5,672,345.

Administration of the vaccine to a bird may be by any known or standard technique, including mucosal or intramuscular injection. Preferred administration methods include oral ingestion or broncho-nasal-ocular spraying. These methods allow the recombinant Salmonella to easily reach the gut-associated lymphoid tissue (GALT) or bronchus-associated lymphoid tissue (BALT) and induce antibody formation and cell mediated immunity. A particularly preferred administration method is to vaccinate newborn birds, e.g., on the day of hatch, by coarse spray.

After growth and harvesting of the recombinant Salmonella strain, the bacterial cells may be lyophilized, particularly if they are to be mixed in foodstuffs. The vaccine comprised of the recombinant Salmonella bacteria may be prepared using any excipient that is pharmaceutically acceptable for the type of bird being immunized. For example, if the vaccine is to be administered in solid form, the cells may be coated with and/or encapsulated in a material that is non-toxic to the inoculated bird and compatible with the bacteria. Solid carriers such as talc or sucrose may also be used. If the administration is to be in liquid form, the cells may be suspended in a suitable liquid carrier, including for example, skim milk, normal saline and/or other non-toxic salts at or near physiological concentrations, and other suitable liquid carriers known to those of skill in the art. Where desirable, adjuvants may also be added to enhance the antigenicity. When the vaccine is intended for administration as a spray, the recombinant Salmonella cells may be suspended in a suitable buffer such as BSG (buffered saline with gelatin, Curtiss III, R., *J. Bacteriol.* 89:28–40, 1965).

The dosage required will vary depending on the quantity and antigenicity of the APEC LPS O-antigen expressed by the recombinant Salmonella strain as well as the type, size and age of bird to be vaccinated. For example, a lower dosage may be required for vaccinating newborn birds than the dosage suitable for vaccinating older birds. Routine experimentation will easily establish the required amount. Generally, the dosage will be in concentrations ranging from $10^5$ to $10^9$ live cells per bird. A preferred dosage for spray vaccination of newborn chickens with vaccines comprising live recombinant *S. typhimurium* cells is about $10^6$ to $10^8$ live cells/bird and a particularly preferred dosage is about $5 \times 10^7$ live cells/bird.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates the construction of an attenuated recombinant *S. typhimurium* strain coexpressing *S. typhimurium* group B LPS and *E. coli* O78 LPS Attenuation strategy. *S. typhimurium* strains carrying deletions in the cya and crp genes have been shown to be attenuated and immunogenic in chickens (Hassan et al., *Res. Microbiol.* 141:839–850, 1990; Porter et al., *Avian Dis.* 37:265–273, 1993) and, in addition, to elicit a protective immune response against wild-type *S. typhimurium* challenge in this species (Hassan et al., supra, Hassan et al., *Infect. Immun.* 62:5519–5527, 1994). Biochemically, deletions in either cya or crp result in an inability to ferment a variety of sugars, including maltose (Botsford et al., *Microbiol. Rev.* 1992). Therefore, Δcya Δcrp *S. typhimurium* vaccine strains form white colonies on MacConkey maltose media, while wild-type *S. typhimurium* strains form red colonies, thus allowing a simple method for discrimination between the vaccine strain and wild-type *S. typhimurium*. Based upon these earlier findings, a Δcya Δcrp *S. typhimurium* was chosen as the carrier strain.

Figure 1:
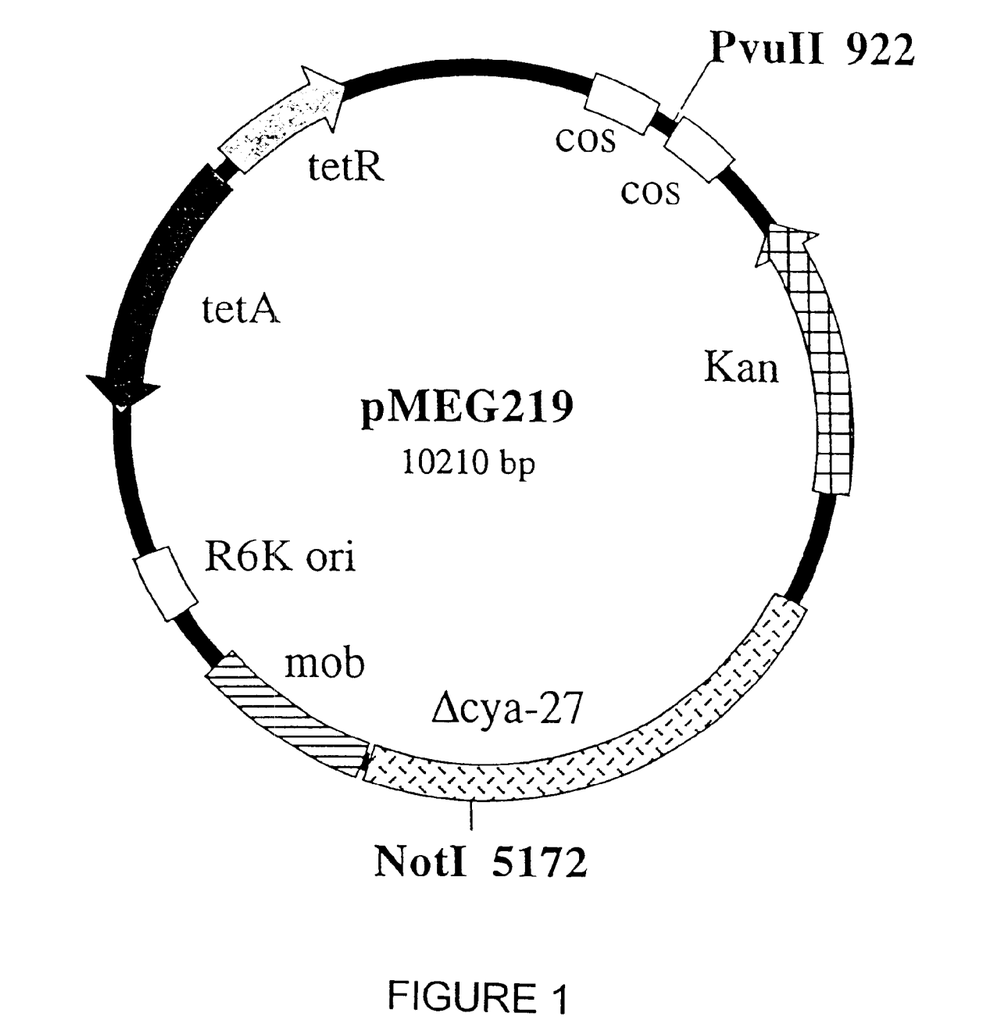
FIG. 1 is a genetic map of the suicide cosmid pMEG219 showing the following features: apir-dependent origin of replication (R6K ori); the tetracycline resistance genes from Tn10 (tetR, tetA); a mobilization fragment from plasmid RK2 (mob), the kanamycin resistance gene (Kan) and double cos sites (cos) from pCOS2EMBL; and the *S. typhimurium* Δcya-27 allele; with the location of NotI and PvuII restriction sites described in the text indicated.

Insertion of the O78 rfb/rfc gene cluster into the Salmonella chromosome. To facilitate the insertion of the O78 rfb into the *S. typhimurium* chromosome and produce an attenuating deletion mutation in the Salmonella cya gene in a single step, a pir-dependent cosmid vector, pMEG219, was constructed. As illustrated in FIG. 1 and in Table 1 below, pMEG219 has the following features: apir-dependent origin of replication, the tetracycline resistance genes from Tn10, a mobilization fragment from plasmid RK2, the kanamycin resistance gene and double cos sites from pCOS2EMBL, and the cloned *S. typhimurium* Δcya-27 allele. Because the origin is pir-dependent, this cosmid can replicate only in special *E. coli* strains that have been engineered to supply the Pir protein (Kolter et al., *Cell* 15:1199–1208, 1978), but not in wild-type *S. typhimurium* strains. The cya-27 allele contains a defined deletion of cya which consists of a 327 bp deletion of the upstream region of cya including the first 13 codons, as well as 476 bp of flanking sequence upstream and 1,826 bp of flanking sequence downstream of the deletion. In addition, a NotI site was engineered at the point of the deletion to facilitate the insertion of DNA in the cya gene (P. Sundarum, personal communication).

TABLE 1

Bacterial strains and plasmids

| Strain | Relevant genotype | Source or reference |
|---|---|---|
| *E. coli* | | |
| χ7122 | avian pathogenic strain O78:K80:H9, nal[r] | Provence et al., Infect. Immun. 60:4460–4467, 1992 |
| MGN026 | endA1 hsdR17 supE44 thi-1 recA1 gyrA relA1 Δ(lacZYA-argF)U169 λpir deoR (φ80ΔlacZM15) | S. Tinge |
| MGN617 | SM10λpir[thi-1 thr-1 leuB6 supE44 tonA21 lacY1 recA RP4-2-Tc::Mu λpir] ΔasdA4 Δzhf-2::Tn10 | this study |
| MGN803 | MGN617(pMEG226) | this study |
| MGN1142 | MGN617(pMEG315) | this study |
| *S. typhimurium* | | |
| χ3761 | UK-1, wild-type | R. Curtiss III |
| MGN394 | Δcya-27 Δcrp-28 | P. Sundaram |
| MGN431 | Δcya-27 Δcrp-28, Mot[+] | P. Sundaram |
| MGN510 | ΔphoP22 pMEG113 integrant | P. Sundaram |
| MGN806 | χ3761 pMEG226 integrant | this study |
| MGN807 | Δcya-28::rfb078 | this study |
| MGN868 | Δcya-28::rfb078 Δcrp-28 | this study |
| MGN996 | Δcya-28::rfb078 Δcrp-28, Mot[+] | this study |
| MGN1175 | MGN431 Δasd::xylE729 (pYA292) | this study |
| MGN1180 | Δcya-28::rfb078 Δcrp-28 Δrfc, Mot[+] | this study |
| MGN1181 | Δcya-28::rfb078 Δcrp-28 Δrfc, Mot[+] | this study |
| MGN1182 | Δcya-28::rfb078 Δcrp-28 Δrfc, Mot[+] | this study |
| MGN1183 | Δcya-28::rfb078 Δcrp-28 Δrfc, Mot[+] | this study |
| MGN1184 | Δcya-27 Δcrp-28 Δrfc, Mot[+] | this study |
| MGN1185 | Δcya-27 Δcrp-28 Δrfc, Mot[+] | this study |
| MGN1717 | MGN1180 Δasd::xylE729 | this study |
| MGN1718 | MGN1717 (pYA292) | this study |
| MGN1720 | MGN1717 (pMEG287) | this study |

TABLE 1-continued

Bacterial strains and plasmids

| Strain | Relevant genotype | Source or reference |
|---|---|---|
| Plasmids | | |
| pYA292 | Expression vector with p15a ori, Ptrc promoter, Asd⁺ | R. Curtiss |
| pYA3255 | pYA3174 (Cosmid cloning vector with pSC101 ori Ap$^r$) carrying rfb from $\chi$7122 | Brown et al., Proc. Nat. Acad. Sci. USA Vol. 93 pp. 11149–11154, 1996 |
| pMEG055 | pYA292 carrying E. coli-derived iutA | this study |
| pMEG113 | pir-dependent suicide vector carrying Δcrp-28, Tet$^r$ | P. Sundaram |
| pMEG219 | pir-dependent "suicide" cosmid vector carrying Δcya-27, Tet$^r$, Kan$^r$ | this study |
| pMEG226 | pMEG219 carrying rfb from $\chi$7122 (Δcya-28::rfbO78) | this study |
| pMEG387 | pYA292 carrying E. coli-derived type I fimbriae | this study |
| pMEG315 | pMEG149 (pir-dependent suicide vector, sacBR, Ap$^r$, provided by S. Tinge) carrying Δrfc | this study |

The O78 rfb/rfc gene cluster was obtained from cosmid clone pYA3255, which contains the rfb region of APEC strain $\chi$7122 (Brown et al., *Proc. Natl. Acad. Sci. U.S.A.* 93:11149–11154, 1996) inserted into the BamHI cloning site of the cosmid vector pYA3174. Restriction analysis of pYA3255 revealed the presence of a NotI site within the cloned $\chi$7122 DNA in addition to two NotI sites that flank the BamHI cloning site (Brown et al., supra). Therefore, cosmid pYA3255 was partially digested with NotI and ligated to NotI/PvuII-digested pMEG219 to yield cosmid pMEG226, which has the rfb region from APEC strain $\chi$7122 inserted into the Δcya-27 allele of cosmid pMEG219. Cosmid pMEG226 was then introduced into the E. coli strain MGN617 by electroporation to produce MGN803 (Table 1). Strain MGN617 has a deletion in the asd gene, which results in a requirement for diaminopimelic acid (DAP) (Schleifer et al., *Bacteriol Rev.* 36:407–477, 1972) and it can support the replication of pMEG226 because it also carries a copy of the pir gene (Table 1).

To introduce cosmid pMEG226 into *S. typhimurium*, the E. coli donor strain MGN803 was mated with wild-type UK-1 *S. typhimurium* strain $\chi$3761 by spotting 50 µl of an aerated overnight culture of each strain onto an LB agar plate (Miller, H., in *Methods in Enzymology*, Vol. 152, p. 147, Berger, S. L. and Kimmel, A. R., eds., Academic Press, Inc. 1987) containing 200 µg/ml DAP and incubating overnight at 37° C. The mating mixture was scraped off of the plate with a sterile wire loop and suspended in 1 ml of BSG. Cells were spread onto LB plates containing 10 µg/ml tetracycline and incubated overnight at 37° C. Counter selection against the donor strain, MGN803, was accomplished by plating on selective media that did not contain DAP. Since cosmid pMEG226 cannot replicate in *S. typhimurium*, the only way recombinant cells can acquire resistance to tetracycline is if the plasmid integrates into the chromosome by homologous recombination. Tetracycline resistant transconjugants were screened for production of O78 LPS by slide agglutination using anti-O78-specific antisera, which was obtained from the E. coli Reference Center at The Pennsylvania State University. One tetracycline resistant, O78⁺isolate, designated MGN806 (Table 1), was grown statically overnight at 37° C. in LB broth and plated onto fusaric acid media (Bochner et al., *J. Bacteriol.* 243:926–933, 1980) to counterselect against the integrated plasmid. Fusaric acid resistant colonies were screened for loss of tetracycline resistance and white color on MacConkey Maltose media. Cya mutants are white on this media because they are unable to ferment maltose (Botsford et al. supra), whereas wild-type *S. typhimurium*, which can ferment maltose, produces red colonies. A tetracycline sensitive, Cya, O78⁺isolate was selected and designated MGN807 (Table 1).

To add a deletion in the Salmonella crp gene, strain MGN807 was transduced with P22 phage grown on strain MGN510 (Table 1) as described previously (Maloy, S. R., *Experimental techniques in bacterial genetics*, Jones and Bartlett, Boston, 1990). MGN510 has integrated into its chromosome the plasmid pMEG113 (Table 1), which is a pir-dependent, tetracycline resistant suicide vector containing the *S. typhimurium* crp gene with a defined deletion mutation. Transductants were selected on LB plates containing 10 µg/ml tetracycline. One transductant was selected and plated onto fusaric acid medium. Fusaric acid resistant isolates were screened for the Crp⁻ phenotype by streaking onto MacConkey Maltose plates containing 2 mM cAMP. On this media, Cya⁻, Crp⁺ strains are red, while Cya⁻, Crp⁻ strains are white. One Δcya::rfbO78 Δcrp isolate was designated MGN868.

Since ΔcyaΔcrp strains are non-motile (Yokota et al., *J. Bacteriol.* 103:513–516, 1970), and because anti-flagella antibodies are known to protect against *S. typhimurium* (Yokoyama et al., *Vaccine* 16:388–393, 1998), MGN868 was passaged through a motility tube (Holt et al., Enrichment and Isolation, in *Methods for General and Molecular Bacteriology*, Gerhardt et al., ed., p. 222, Am. Soc. for Microbiol., Washington, D.C.) filled with motility agar (Difco) to yield a motile variant of MGN 868, which was designated MGN996 (Table 1).

Figure 2A:
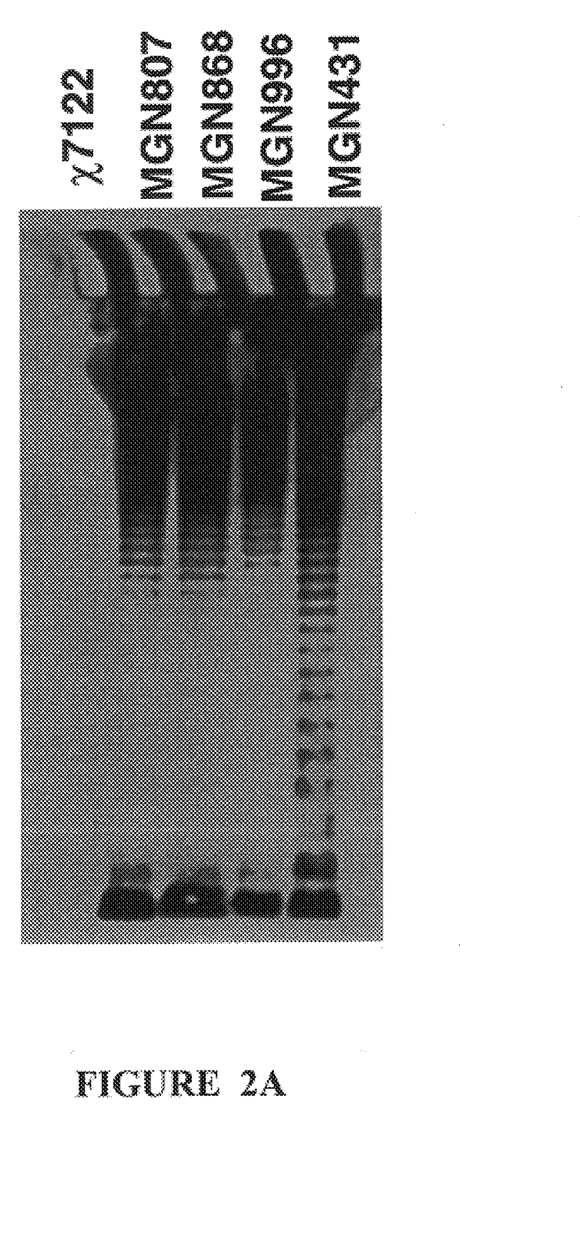

The LPS expressed by MGN807, MGN 868, and MGN996 was examined by SDS-PAGE and western blot as follows. Cells of each of these strains, as well as of $\chi$7122 and MGN431 (Table 1) as controls for O78 LPS and *S. typhimurium* group B LPS, respectively, were grown overnight in LB broth. Cells were adjusted to an equivalent $OD_{600}$ and 1 ml of each culture was pelleted by centrifugation. LPS was prepared from the pelleted cells by the method of Hitchcock and Brown (*J. Bacteriol.* 154:269–277, 1983). Samples were run on duplicate 12.5% SDS polyacrylamide gels, transferred to a nitrocellulose membrane, and probed with anti-Group B-specific antisera (Difco) or anti-O78-specific antisera as described (ECL *Western Blotting Protocols*, p. 16–17, Amersham Life Science, 1997). The results are shown in FIG. 2.

Figure 2B:
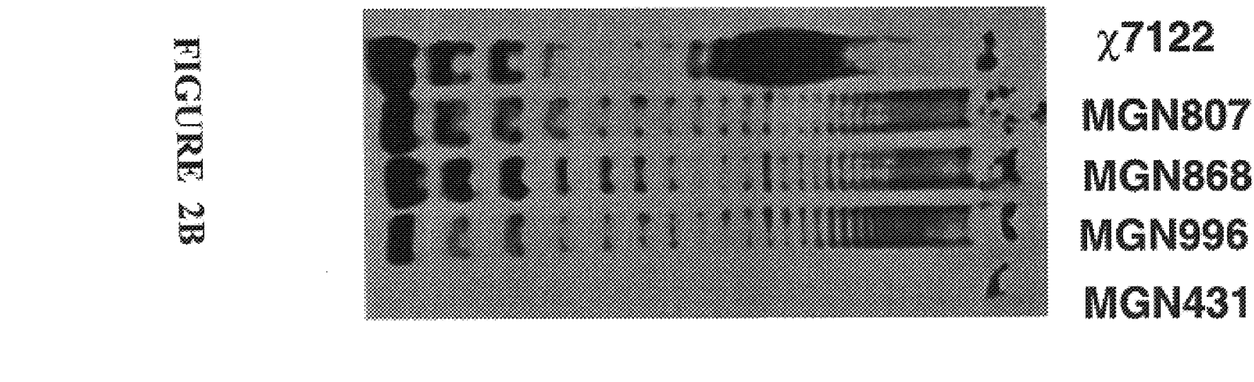

As expected, LPS isolated from the *E. coli* strain χ7122 did not react with anti-Group B antibody (FIG. 2A) but did react with the anti-O78 antibody (FIG. 2B). Similarly, the *S. typhimurium* control strain MGN431 (cya-27 crp-28, Mot$^+$) made LPS that reacted with anti-Group B antibody (FIG. 2A) but did not react with the anti-O78 antibody (FIG. 2B). However, LPS isolated from the recombinant *S. typhimurium* strains MGN807, MGN868 and MGN996 reacted with both antibodies (FIGS. 2A, 2B) to produce distinctive ladder patterns of high molecular weight bands, indicating these strains express both *S. typhimurium* group B and *E. coli* O78 O-antigen attached to the Salmonella core. The expression of high molecular weight O78 LPS by the recombinant Salmonella strains also indicates that the cloned χ7122 rfb region in plasmid pYA3255 also contains the rfc gene of χ7122.

Figure 3A:
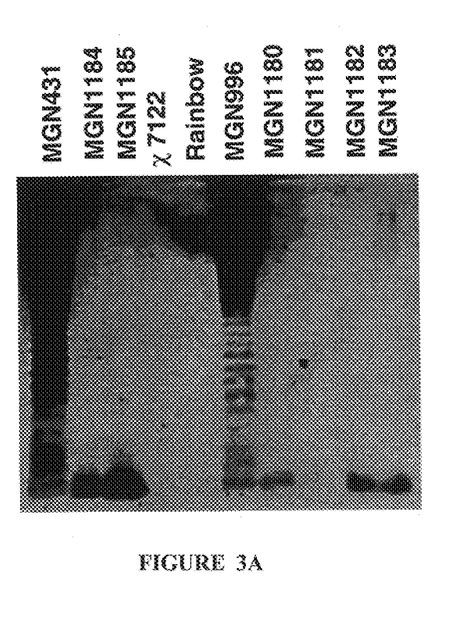
Figure 3B:
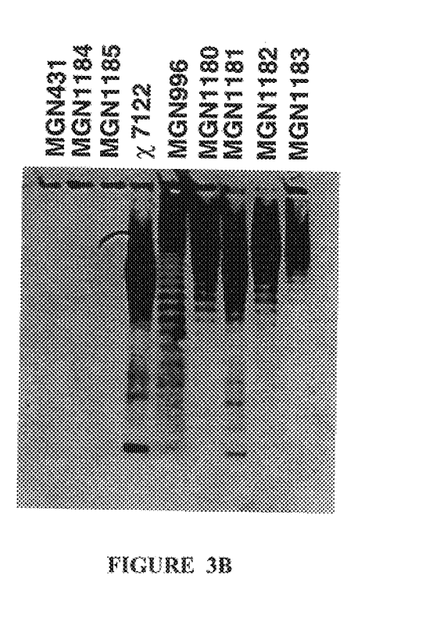

The average chain length for the O78 LPS expressed in the recombinant *S. typhimurium* strains was approximately the same size as the average chain length of the group B LPS expressed in the same strain (compare MGN807, MGN868 and MGN996 lanes in FIGS. 3A and 3B), while O78 expression in χ7122 resulted in a shorter chain length (FIG. 3B). There is a gene whose product is known to regulate LPS chain length which has been assigned several different names by different groups, cld (Bastin et al., *Mol. Microbiol.* 7:724–734, 1993; Bastin et al., *Mol. Microbiol.* 5:2223–2231, 1991), rol (Batchelor et al., *J. Bacteriol.* 174:5528–5236, 1992; Batchelor et al., *J. Bacteriol.* 173:5699–5704, 1991), and, more recently, wzz (Reeves et al., *Trends Microbiol.* 4:495–503, 1996). It is likely that in recombinant *S. typhimurium* strains MGN807, MGN 868, and MGN996, the O78 LPS chain length is determined by the *S. typhimurium* wzz gene.

EXAMPLE 2

This example illustrates the ability of the recombinant *S. typhimurium* strain MGN996 (Δcya-28::rfbO78, Δcrp-28, Mot$^+$) to colonize chickens and protect them from challenge with the wild-type APEC strain χ7122.

All chickens used in the experiments described in Examples 2–4 were White Leghorns hatched from fertile eggs from specific-pathogen-free (SPF) chickens obtained from Specific Pathogen Free Avian Services (SPAFAS, Roanoke, Ill.). The eggs were incubated and hatched in a Humidaire incubator/hatcher located in the Department of Biology at Washington University in St. Louis, Mo.

In this experiment birds were vaccinated twice: once at day-of-hatch and again at 14 days of age. Chicks were inoculated at day-of-hatch with 4.6×10$^6$ CFU of MGN996 per chick by coarse spray. Coarse spray vaccination was performed by placing 10–15 chicks into a Plexiglas spray box and delivering the inoculum using a stainless steel Sure Shot Model A sprayer (Milwaukee Sprayer Manufacturing Co., Inc., Milwaukee, Wis.) pressurized to 100 psi. Practice trials were performed in advance to determine the appropriate conditions to deliver 0.3 ml/chick. Twenty six chicks were vaccinated with MGN966 and twelve chicks were mock vaccinated with BSG. After inoculation, the chicks were transferred to Horsfall isolators and provided food and water ad libitum after day of hatch vaccinations.

At day 10, three chicks, chosen at random from the vaccinated group, were euthanized by CO$_2$ inhalation and then immediately necropsied to assess colonization. Samples of lung, liver, spleen, bursa of Fabricius and cecal contents were taken from each bird, placed into individual stomacher bags, and 5 ml of BSG was added to each sample. Tissues were homogenized in a Seward Stomacher 80 Laboratory Blender. Then, 0.1 ml of homogenized sample was plated onto MacConkey agar base (Difco) supplemented with 1% maltose, for spleen, liver and lung, or Brilliant Green agar (Difco) containing 35 μg/ml novobiocin for bursa of Fabricius samples and cecal contents. Plates were incubated overnight at 37° C. At least one typical colony from each plate was further analyzed to confirm expression of the appropriate LPS type(s) by slide agglutination. For cases in which no colonies were obtained from direct plating, 0.5 ml of homogenized tissue sample was added to 4.5 ml Hajna broth and incubated overnight at 42° C. as a secondary enrichment. A loopful of the Hajna-enriched culture was streaked onto Brilliant Green Agar and incubated overnight at 37° C. The MGN996 strain was found in samples of all tissues examined.

On day 14, vaccinated birds were boosted with 3.8×10$^7$ CFU of MGN996 in a volume of 0.2 ml by oral gavage using a feeding cannula attached to a 1 cc syringe. On day 28, all birds were challenged with 7.5×10$^7$ CFU of *E. coli* strain χ7122 in a volume of 0.5 ml by the intratracheal route and four days later were euthanized by CO$_2$ inhalation and then necropsied.

The necropsied birds were scored for lesions associated with APEC infection. In this experiment and those described in Examples 3–4, analysis of the lesion scores was done using the Wilcoxon-Mann-Whitney U test (Zar, J. H., *Biostatistical Analysis*, Prentice-Hall, Inc., Englewood Cliffs). In this experiment, a $\chi^2$ analysis was used to determine differences between groups based on the number of birds showing no lesions (lesion score of 1) and the results are shown below in Table 2.

TABLE 2

Mean lesion scores of chickens vaccinated with MGN996 vs non-vaccinates after challenge with APEC strain χ7122[1].

| Group | # of Birds with Each Lesion Score | | | | | Mean Score[2] |
|---|---|---|---|---|---|---|
| | 1 | 2 | 3 | 4 | 5 | |
| BSG | 1 | 0 | 1 | 8 | 2 | 3.8[a] |
| MGN996 | 10 | 2 | 1 | 7 | 1 | 2.4[b] |

[1]Birds were scored as follows: 1. live birds, no lesions 2. Live bird with cloudy air sacs 3. Live bird with only one type of lesion (e.g. perihepatitis only) 4. Live bird with multiple lesions 5. Dead or moribund bird with lesions typical of colibacillosis (perihepatitis, pericarditis, air sacculitis, severe dehydration).
[2]a different from b (p = 0.0157)

The mean lesion scores indicate that birds vaccinated with MGN996 were significantly protected from challenge when compared to non-vaccinated control birds ($\chi^2$=5.3, p=0.02). In addition, the vaccinated group showed a significant reduction in overall mean lesion scores (p=0.0157). These results show that delivery of *E. coli* LPS by an attenuated *S. typhimurium* also expressing group B O-antigen provides chickens with significant protection from challenge with wild-type *E. coli*.

EXAMPLE 3

This example illustrates the effect of removing expression of the Salmonella O-antigen on the ability to colonize various chick tissues.

To eliminate expression of group B O-antigen by the recombinant *S. typhimurium* vaccine strain, a defined deletion was made in the Salmonella rfc gene of MGN996 (Δcya::O78 Δcrp; Table 1) and MGN43 1 (a defined Δcya Δcrp deletion control strain, Table 1). Strain MGN996 or MGN431 was mated with strain MGN1142 (Table 1) essentially as described in Example 1 with selection for ampicillin resistance. MGN1142 contains apir-dependent suicide vector carrying an S. typhimurium mutant rfc gene. A transconjugant from each mating was grown overnight in LB broth containing 50 μg/ml ampicillin and plated onto LB agar plates minus NaCl supplemented with 5% sucrose and incubated for 48 hours at room temperature. Isolates were screened for the Rfc phenotype by cross streaking against P22 phage. As discussed above, in this assay mutants deficient in S. typhimurium O-antigen polymerase are resistant to P22, while isolates expressing functional S. typhimurium O-antigen polymerase are sensitive.

Several independent $\Delta rfc_{St}$ (denotes the rfc gene of S. typhimurium) isolates were obtained and designated MGN1180, MGN1181, MGN1182, and MGN1183, which are derived from MGN996; and strains MGN1184 and MGN1185, which are derived from the Δcya Δcrp S. typimurium strain MGN431. See Table 1. The LPS made by these strains was isolated and analyzed for group B and O78 O-antigen by western blot as described above in Example 1 and the results are shown in FIG. 3.

As expected, LPS made by the Δcya Δcrp control strain MGN431 and its $\Delta rfc_{St}$ derivatives MGN 1184 and MGN1185 reacted with anti-group B LPS antibody (FIG. 4A) and did not react with anti-O78 LPS antibody (FIG. 4B). However, the LPS isolated from the $\Delta rfc_{St}$ strains produced only low molecular weight species when probed with anti-group B LPS antibody (FIG. 4A) indicating they did not express full-length group B LPS. When probed with anti-O78 LPS antibody, LPS made by MGN996 and its $\Delta rfc_{St}$ derivative strains (MGN1180, MGN1181, MGN1182, and MGN1183) produced a pattern indicative of complete O78 E. coli O-antigen (FIG. 4B). The O78-specific LPS pattern in strain MGN1180 (FIG. 4B) was similar to the group B LPS chain length in MGN996 (FIG. 4A), while the O78-specific LPS pattern in MGN1181 (FIG. 4B) was more similar to the O78 LPS pattern seen in the wild-type O78 E. coli strain, χ7122 (FIG. 4B). The difference in LPS patterns was unexpected, since the two strains have apparently identical genotypes (Table 1). Strains MGN1180, MGN1181 and MGN1184 were chosen for further study as possible vaccines against E. coli χ7122.

Ten chicks per strain were inoculated at day-of-hatch by oral gavage with MGN996 (6.9×10⁷ CFU/chick), MGN1180 (4.0×10⁷ CFU/chick), MGN1181 (2.4× 10⁷ CFU/chick), MGN1184 (1.3×10⁷ CFU/chick), or MGN431 (7.8×10⁷ CFU/chick). The vaccinated birds were placed into isolators and necropsied at day 10 as described above. Samples of lung, liver, spleen, bursa of Fabricius and cecal contents were collected, processed and assessed for colonization as described in Example 2 and the results are shown in Table 3 below.

TABLE 3

Colonization of chickens by recombinant Δcya Δcrp Δrfc S. typhimurium vaccine candidates and control strains (% birds positive)

| Strain | Genotype | Lung | Spleen | Liver | Bursa | Ceca |
| --- | --- | --- | --- | --- | --- | --- |
| MGN996 | cya::rfb 078 Δcrp | 100% | 100% | 100% | 100% | 100% |
| MGN1180 | cya::rfb 078 ΔcrpΔrfc | 80% | 100% | 100% | 100% | 100% |
| MGN1181 | cya::rfb 078 ΔcrpΔrfc | 70% | 100% | 100% | 100% | 100% |
| MGN1184 | ΔcyaΔcrpΔrfc | 20% | 50% | 70% | 100% | 100% |
| MGN431 | ΔcyaΔcrp | 77% | 100% | 66% | 100% | 100% |

The results indicate that all of the $\Delta rfc_{St}$ strains tested, except MGN1184, are capable of colonizing a large percentage of the birds' lung, spleen, liver, bursa of Fabricius and ceca. Like control strains MGN431 and MGN996, strains MGN1180 and MGN1181 were found to colonize 100% of the spleens of vaccinated birds. Strain MGN1184 has a semi rough phenotype due to the Δrfc mutation. It has been reported that LPS-deficient S. typhimurium strains exhibit reduced colonization of chickens (Craven et al., Avian Dis. 38:401–408, 1994). Bird to bird variation not withstanding, the results obtained in this experiment were consistent with the fact that colonization by MGN1184 was severely impaired, confirming a role of complete LPS O-antigen in colonization. However, expression of O78 E. coli O-antigen in an Rfc background (MGN1180 and MGN1181) resulted in a significant increase in the percentage of birds colonized when compared to MGN1184, suggesting that it would be useful to evaluate these strains for their ability to protect against E. coli challenge.

EXAMPLE 4

This example illustrates the efficacy of a recombinant S. typimurium strain which expresses O78 E. coli O-antigen but does not express group B O-antigen in protecting chicks against disease caused by infection with the O78 APEC strain, χ7122.

Thirty-five chicks per strain were inoculated at day-of-hatch by oral gavage with either 6.5×10⁷ CFU of MGN996 (Δcya-28::rfbO78 Δcrp-28, Mot⁺) or 7.7×10⁷ CFU of MGN1180 (Δcya-28::rfbO78 Δcrp-28 Δrfc, Mot⁺). Twenty chicks were mock vaccinated with BSG. At day 10, five chicks from each inoculated group were necropsied to assess colonization as described in Example 2. The colonization results were similar to those seen in Experiment 2 (data not shown). On day 14, birds previously inoculated with MGN996 were boosted with 7.4×10⁷ CFU of MGN996 and birds previously vaccinated with MGN1180 were boosted with 6.4×10⁷ CFU of MGN1180. All birds were leg banded on day 24. To assess post-vaccination serum antibody responses, serum was collected by wing vein puncture from half of the birds on day 27 and the other half on day 28. Half the birds in each group were challenged on day 30 and the remaining birds were challenged on day 31. The challenge dose was 9.6×10⁷ CFU of E. coli strain χ7122. Two control birds died prior to bleeding, so only 18 control birds were bled and challenged. Necropsies were performed on all birds four days post-challenge to assess colonization by χ7122 as described in Example 2, except that heart blood was also collected. The challenge strain was isolated from all birds, but was primarily found only in the ceca of birds vaccinated with MGN996 or MGN1180. Lesion scoring data from the two necropsy days were pooled for analysis and the results are shown in Table 4 below.

TABLE 4

Mean lesion scores of chickens vaccinated with S. typhimurium strains MGN996, MGN1180 or non-vaccinates after challenge with APEC strain χ7122[1].

| Treatment | # of Birds with Each Lesion Score | | | | | Mean Lesion Score[1] |
|---|---|---|---|---|---|---|
| | 1 | 2 | 3 | 4 | 5 | |
| None | 0 | 4 | 6 | 8 | 0 | 3.2[a] |
| MGN996 | 9 | 8 | 8 | 5 | 0 | 2.3[b] |
| MGN1180 | 14 | 10 | 4 | 2 | 0 | 1.8[c] |

[1]Lesions scores were determined as described in Table 2.
a different from b, p = 0.0064
a different from c, p < 0.0001

The results confirm the efficacy of strain MGN996 and indicate that MGN1180 may be a superior *E. coli* vaccine, since the mean lesion score for birds vaccinated with MGN1180 are lower than the mean lesion score for MGN996 vaccinates, although the difference was not significant (p=0.08).

Serum from each bird was evaluated for antibody responses directed against *E. coli* O78 LPS and *S. typhimurium* LPS by enzyme-linked immmunosorbent assay (ELISA). Wells of an Immulon-I flat bottom plate were coated with 100 µl of either *E. coli* LPS (Sigma) or *S. typhimurium* LPS (Sigma) prepared at 2.5 µg/ml in 0.2% TCA (tricholoroacetic acid; Sigma) for 2 hours at 37° C. (Hardy, 1994). Following coating, the plate was washed three times with a TBS (Tris Buffered Saline)/0.1% tween 20 solution. Diluted sera (1:100) were added to duplicate wells and the plate incubated at 37° C. for 1 hour. This step was followed by three washes with TBS/0.1% tween 20 solution. Bound IgG was detected by the addition of a 1:30,000 diluted goat anti-chicken IgG HRP conjugated antibody (KPL). Plates were again washed with TBS/0.1% tween 20 to remove unbound detection antibody. Washing was followed by development with OPD (o-phenlyenediamine dihydrocholoride) tablets (Sigma) in phosphate-citrate buffer with sodium perborate. After 15 minutes at 37° C., the reaction was stopped by the addition of 3N HCl to each well. Plates were read at 490 nm using a BT2000 Microkinetics Reader (FisherBiotech). To detect bound IgM and IgA, the plate was first blocked using 1:5 diluted normal rabbit sera for 45 minutes at 37° C. followed by three washes of TBS/0.1% tween 20. After blocking, 1:5000 diluted goat anti-chicken IgM or IgA (Immunovision) was added to each well and the plate incubated at 37° C. for an additional 45 minutes. After three washes in TBS/0.1% tween 20 to remove the unbound antibody, 1:5000 diluted rabbit anti-goat IgG alkaline phosphate conjugated antibody (Sigma) was added to each well. The plate was again incubated at 37° C. for 45 minutes. After removal of unbound conjugated antibody, a detection step of p-NPP (P-nitrophenylphosphate in diethanolamine; Sigma) substrate solution was added to each well and the plate incubated for 30 minutes at 37° C. The reaction was then stopped by the addition of 3M NaOH and the plate read at 405 nm. Birds were considered seropositive if an OD value greater than 0.2 was observed. Controls included prebleeds from 12 birds and wells containing conjugated antibody only. The results are shown in Tables 5 and 6 below.

TABLE 5

Percent Seropositive for O78 LPS, Pre- and Post-challenge

| | TREATMENT GROUPS | | | | | |
|---|---|---|---|---|---|---|
| | Controls | | MGN996 (Rfc+) | | MGN1180 (Rfc) | |
| Isotype | Pre | Post | Pre | Post | Pre | Post |
| IgM | 0 | 88 | 53 | 100 | 80 | 97 |
| IgG | 0 | 17 | 20 | 77 | 57 | 83 |
| IgA | 0 | 17 | 30 | 87 | 70 | 87 |

TABLE 6

Percent Seropositive for group B LPS, Pre- and Post-challenge

| | TREATMENT GROUPS | | | | | |
|---|---|---|---|---|---|---|
| | Controls | | MGN996 (Rfc+) | | MGN1180 (Rfc) | |
| Isotype | Pre | Post | Pre | Post | Pre | Post |
| IgM | 0 | 17 | 93 | 100 | 30 | 57 |
| IgG | 0 | 6 | 27 | 67 | 7 | 17 |
| IgA | 0 | 0 | 70 | 87 | 10 | 20 |

Approximately 50% of the birds vaccinated with MGN996 were seropositive for O78-specific IgM antibodies, while only 20–30% were positive for O78-specific IgG and IgA antibodies pre-challenge. By contrast, 80% of the birds vaccinated with the $Rfc_{St}^-$ strain, MGN1180, were positive for O78-specific IgM antibodies pre-challenge, with 57% and 70% of the birds seropositive for IgG and IgA O78-specific antibodies, respectively. These results indicate a further maturation of humoral immune responses generated by vaccination with MGN1180 than with the $Rfc_{St}^+$ strain MGN996. Although post-challenge seroconversion was similar between the groups, the $OD_{405}$ values of 85% (22/26) of the IgA seropositive birds vaccinated with MGN1180 were greater than 0.5 as compared to only 42% (11/26) of the birds vaccinated with MGN996. The high percentage of mock-vaccinated birds seropositive for anti-O78 IgM may be due to restimulation of memory B cells reactive to a common *E. coli* antigen present in the O78 LPS preparation (e.g. LPS core). As expected, MGN996 vaccinates gave a stronger humoral antibody response to *S. typhimurium* LPS than did MGN1180 vaccinates, since MGN1180 produces *S. typimurium* LPS having only a single sugar unit of the O-antigen, which may be masked by the O78 LPS. This speculation is based upon the observation that strain MGN1180 does not agglutinate in the presence of group B specific antisera, while strain MGN1184 (Δcya Δcrp Δrfc) does agglutinate, albeit more weakly than a *S. typhimurium* strain expressing complete LPS O-antigen.

Overall there was a strong correlation between a robust pre-challenge antibody response and a low lesion score, although there were a few birds that did not mount a detectable pre-challenge antibody response that were protected, and there were a few birds that mounted a detectable pre-challenge antibody response but were scored as not being protected. Most of the birds vaccinated with MGN1180 were seropositive for O78 antibodies (24/30) before challenge, while fewer birds (17/30) from the MGN996 group were seropositive.

EXAMPLE 5

This example illustrates the vaccination of chicks with a recombinant vaccine *S. typhimurium* strain also containing an Asd+vector that can be used to express additional heterologous gene products.

The Asd+vector pYA292 (Table 1) was introduced into MGN1717 (Table 1) by electroporation to produce strain MGN1718 [(Δcya-28::rfbO78 Δcrp-28 Δrfc1 Δasd::xylE729)/pYA292, Mot+]. The chickens used in this Example were all hatched from fertile eggs from specific-pathogen-free (SPF) chickens obtained from Sunrise Farms (Catskill, N.Y.). Twenty chicks were mock-vaccinated with BSG and 29 chicks were vaccinated at day-of-hatch with $5.6 \times 10^7$ CFU of MGN1718 by oral gavage as described above. On day 14, vaccinated birds were boosted with $5.2 \times 10^7$ CFU of MGN1718 by oral gavage and on day 28 all birds were challenged with $5 \times 10^7$ CFU of $\chi$7122 as described above. Four days later the birds were euthanized, necropsied, and scored for lesions as described above except a new, more sensitive scoring system was used, which is listed in Table 7 below and the mean lesion scores using this scoring system are shown below in Table 8.

TABLE 7

Method for scoring lesions

| Air sacs (thoracic) | |
| --- | --- |
| Normal | 0 |
| Mild cloudiness and thickness | 1 |
| Moderate cloudiness, and thickness accompanied by serous exudates and fibrin spots | 2 |
| Extensive cloudiness and thickness accompanied by muco- or fibrino-purulent exudate | 3 |
| Heart and pericardium | |
| Normal | 0 |
| Turbidity and presence of excessive fluid in the pericardial cavity | 1 |
| Acute pericarditis | 2 |
| Liver | |
| Normal | 0 |
| Decolorized and/or slight amounts of fibrinous exudates | 1 |
| Marked perihepatitis | 2 |
| Bacteriological examinations | |
| Re-isolatioll of E. coli | |
| after incubating air sac-swabbed sample in BHI | 1 |
| from direct streak for air sacs | 2 |
| after incubating pericardial fluid- or heart-swabbed sample in BHI | 1 |
| from direct streak from pericardial or heart sample | 2 |
| from incubating liver-swabbed sample in BHI | 1 |
| from direct liver streak | 2 |

Maximum possible points per bird = 13.

TABLE 8

Mean Lesion Scores for $\chi$7122 challenge

| Treatment | # of Birds with each Lesion Score | | | | | | | | | | Mean Lesion Score[1] |
| --- | --- | --- | --- | --- | --- | --- | --- | --- | --- | --- | --- |
| | 0 | 1 | 2 | 3 | 4 | 5 | 6 | 7 | 8 | 9 | |
| Non-vac | 1 | 2 | 1 | 2 | 2 | 2 | 2 | 2 | 2 | 4 | 5.30[a] |
| MGN1718 | 8 | 8 | 9 | 1 | 1 | 0 | 0 | 2 | 0 | 0 | 1.62[b] |

[1] a different from b (p < 0.0001)

To assess whether the *S. typhimurium* carrier strain is contributing to the protection against challenge with the APEC strain, a very similar experiment was done using MGN1175 (Table 1), which is genetically very similar to MGN1718 but lacks the O78 rfb gene cluster. The mean lesion scores for mock-vaccinated controls or vaccinated birds following challenge with $7.5 \times 10^7$ CFU of $\chi$7122 are shown in Table 9 below.

TABLE 9

Mean Lesion Scores for $\chi$7122 challenge

| Treatment | # of Birds with each Lesion Score | | | | | | | | | | Mean Lesion Score |
| --- | --- | --- | --- | --- | --- | --- | --- | --- | --- | --- | --- |
| | 0 | 1 | 2 | 3 | 4 | 5 | 6 | 7 | 10 | 11 | |
| Non-vac | 3 | 1 | 2 | 2 | 2 | 6 | 2 | 1 | 0 | 1 | 3.95 |
| MGN1175 | 3 | 3 | 4 | 8 | 2 | 6 | 1 | 1 | 2 | 0 | 3.53 |

The mean lesion score for vaccinated birds was not significantly different than that for the mock-vaccinated control birds. This result indicates that the protection against the APEC $\chi$7122 strain provided by the recombinant *S. typhimurium* vaccine strains MGN1718 and MGN1180 strains was due to the expression of O78 *E. coli* O-antigen.

EXAMPLE 6

This example illustrates the construction and efficacy of one embodiment of the O-78 vaccine strain which also expresses a fimbrial operon of an O1:K1:H7 APEC strain.

Figure 4:
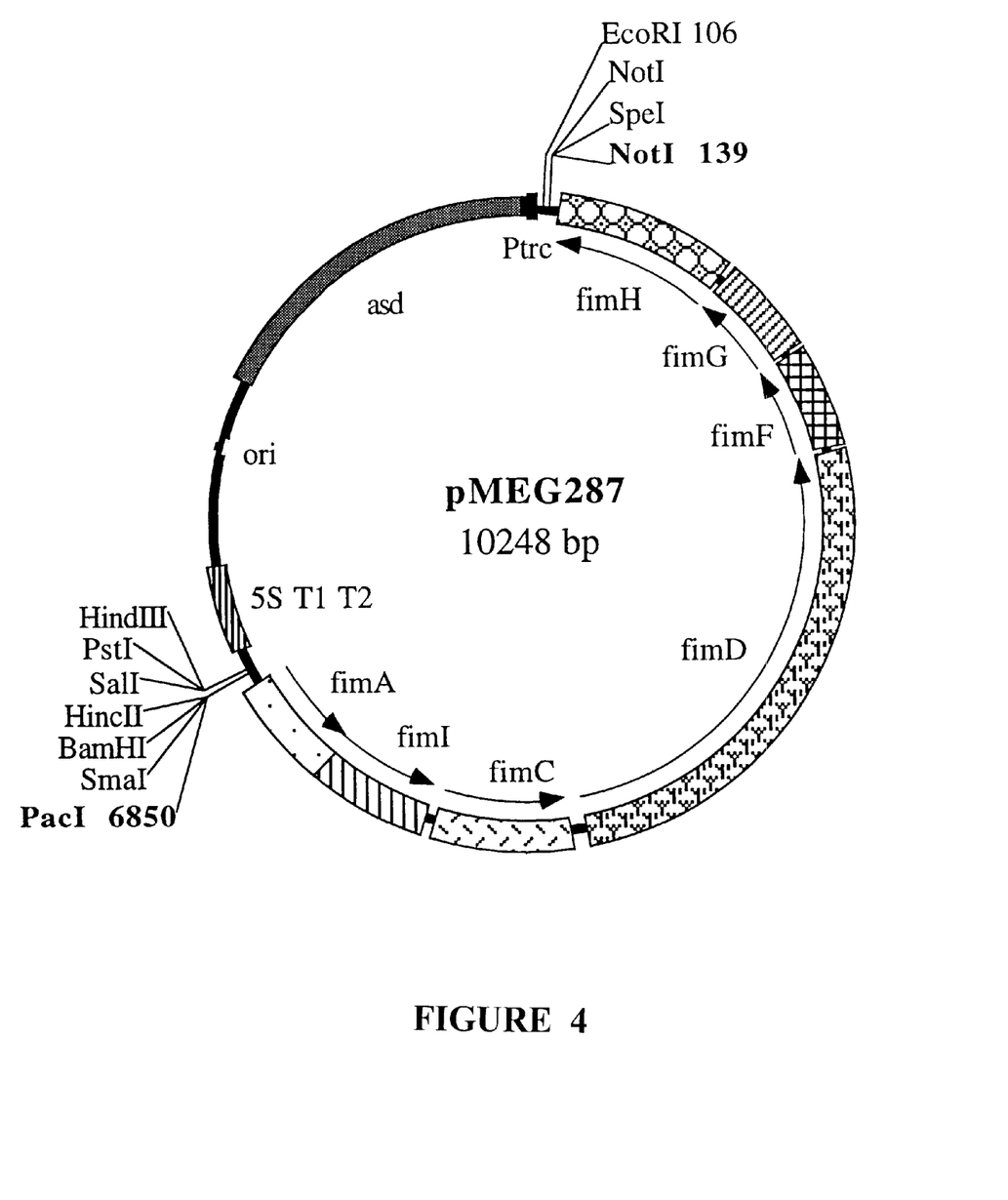
FIG. 4 is a genetic map of pMEG287 showing the location of genes discussed in the text.

Fimbrial operons are cell surface structures which have been associated with virulence in APEC strains (Dozios et al., *Infect. Immun.* 60:2648–2656, 1992; Dozios, et al., *Avian Dis.* 38:231–239, 1994; Wooley et al., *Av. Dis.* 36:679–684, 1992), and type I fimbriae, in particular, have been implicated important for colonization of avian tracheal epithelial cells by avian pathogenic *E. coli* (APEC) strains (Gyimah et al., *Avian Dis.* 32:74–78, 1988). The genes involved in type 1 fimbriae production have been cloned from an O1:K1:H7 APEC isolate, inserted into an Asd+ plasmid vector (pYA292) and expressed constitutively. A genetic map of the resulting plasmid, pMEG287, is shown in FIG. 4. Plasmid pMEG287 was introduced into the recombinant *S. typhimurium* strain MGN1717 (Table 1), to yield MGN1720 ([Δcya-28:rfb O78 Δcrp-28 Δrfc Δasd::xylE729]/pYA292, Mot+. Expression of type I fimbriae in strain MGN1720 was confirmed by a yeast agglutination assay (Korhonen, T. K., *FEMS Micrbiol. Lett.* 6:421–425, 1979), using aerated overnight cultures grown at 37° C. Agglutination was mannose-sensitive, as expected for type I fimbriae, and the control strain, MGN1718, did not agglutinate yeast cells. Although wild-type *S. typhimurium* strains express type I fimbriae, the result with strain MGN1718 is consistent with the fact that expression of type I fimbriae expression is regulated by Δcya Δcrp, and are therefore only poorly expressed in Cya⁻Crp⁻ strains (Saier et al., *J. Bacteriol.* 134:356–358, 1978), and only after two days of static growth at 37° C.

The efficacy of strains MGN1718 and MGN1720 were evaluated in chickens essentially as described above using a challenge dose of $5 \times 1^7$ CFU and the results are shown below in Table 10.

TABLE 10

Mean Lesion Scores for χ7122 challenge

| Treatment | # of Birds with each Lesion Score | | | | | | | | | | Mean Lesion Score[1] |
|---|---|---|---|---|---|---|---|---|---|---|---|
| | 0 | 1 | 2 | 3 | 4 | 5 | 6 | 7 | 8 | 9 | |
| Non-vac | 1 | 2 | 1 | 2 | 2 | 2 | 2 | 2 | 2 | 4 | 5.30[a] |
| MGN1718 | 8 | 8 | 9 | 1 | 1 | 0 | 0 | 2 | 0 | 0 | 1.62[b] |
| MGN1720 | 6 | 16 | 6 | 0 | 0 | 1 | 0 | 0 | 0 | 0 | 1.14[b] |

$p < 0.0001$
[1] a different from b ($p < 0.0001$)

These results show that the addition of type I fimbriae results in lower lesion scores, although not statistically significant. While the addition of type I fimbriae to the vaccine strain did not enhance protection against O78 challenge, it may provide cross-protection against other APEC serotypes.

Other fimbriae that may be used are P type fimbriae, including F11, which have been associated with APEC strains (van den Bosch, et al., *Infect. Immun.* 61:800–806, 1993).

EXAMPLE 7

This example illustrates the construction of an embodiment of the O78 vaccine strain which also expresses an *E. coli* iron-regulated outer membrane protein.

The ability to scavenge iron is an important survival trait for pathogens because the availability of iron is limiting in the animal host environment (Litwin et al., *Clin. Microbiol. Rev.* 6:509–518, 1993; Peighambari, et al., *Avian Dis.* 39:116–124, 1995). A number of iron-responsive genes encode outer membrane proteins (OMPs), with most of these acting as receptors for iron-chelating compounds (siderophores) produced by the bacteria or the host (Bagg, et al., *Microbiol. Rev.* 51:509–518, 1987).

Iron-regulated OMPs are antigenic and antibodies against *E. coli* iron-regulated OMPs have been detected in healthy humans, rabbits, mice and guinea pigs (Griffiths, et al., *Infect. Immun.* 47:808–813, 1985). Antibodies raised against *E. coli* iron-regulated OMPs passively protect turkeys against subsequent challenge with an avian pathogenic O78 *E. coli* (Bolin, et al., *Infect. Immun.* 55:1239–1242, 1987), indicating that these proteins are protective antigens.

An excellent candidate for a vaccine antigen is the iron-responsive 78-kDa OMP IutA. IutA is the receptor for aerobactin and cloacin (Bagg, et al., *Microbiol Rev.* 51:509–518, 1987). Synthesis of aerobactin is directly correlated with *E. coli* virulence in humans and mammals (Litwin et al., *Clin. Microbiol. Rev.* 6:509–518, 1993; Payne, S. M., *Crit. Rev. Microbiol.* 16:81–111, 1988.), as well as in poultry (Dho et al., *Avian Dis.* 28:1016–1025, 1984; Emery et al., *Avian Dis.* 36:504–511, 1992; Lafont et al., *Infect. Immun.* 55:193–197, 1987, Linggood et al., *J. Gen. Microbiol.* 133:835–842, 1987; Wooley et al., *Av. Dis.* 36:679–684, 1992). Aerobactin is a component of a high affinity iron uptake system (Bagg, et al., *Microbiol. Rev.* 51:509–518, 1987), which may account for its prevalence among pathogenic organisms. A number of studies of avian *E. coli* isolates have found that greater than 80% of pathogenic isolates produce aerobactin (Dho et al., supra; Emery et al., supra; Lafont et al., supra; Yokoyama et al., supra), while it is rare among non-pathogenic strains. The genes for aerobactin synthesis are most often found on ColV plasmids, and therefore are tightly liked to colicin V production (Bagg et al., supra).

Figure 5:
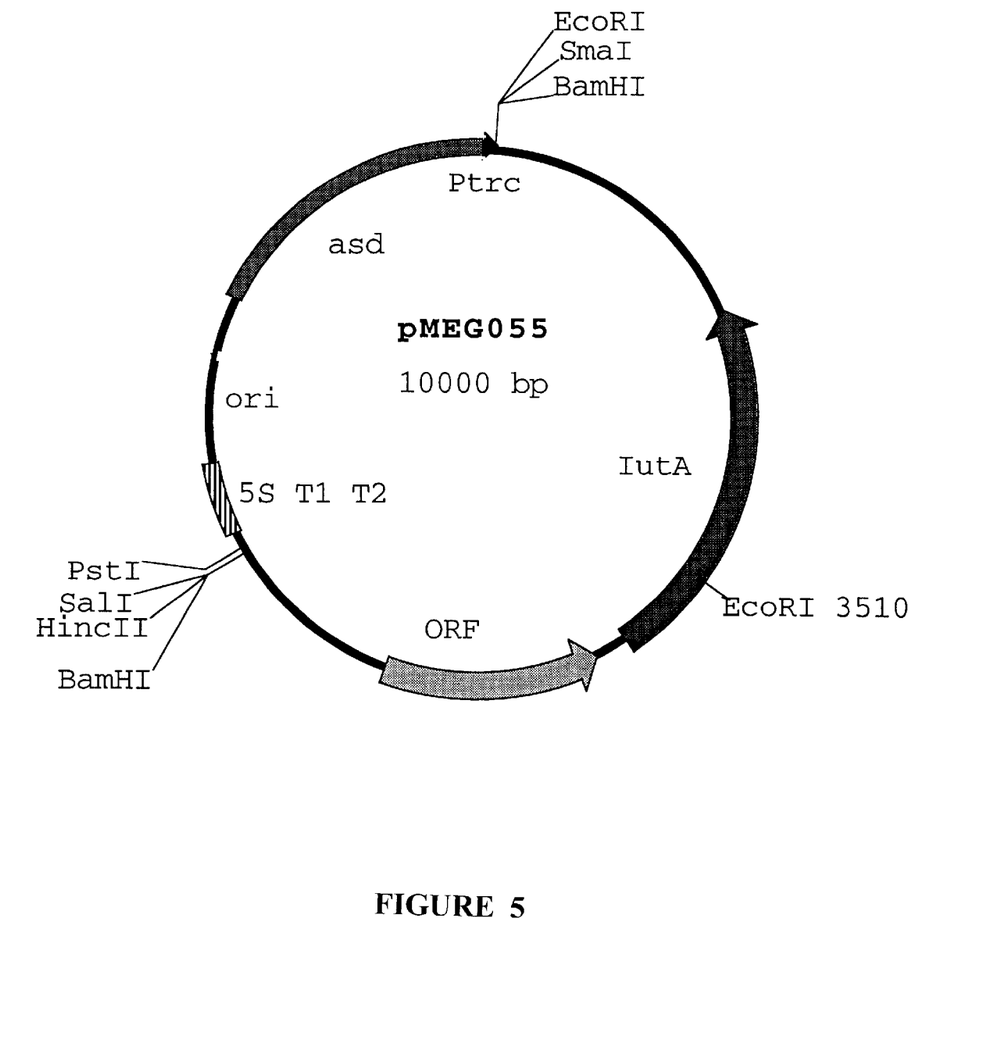
FIG. 5 is a genetic map of pMEG055 showing the location of genes discussed in the text.

An IutA clone from pColV-K30 is available as plasmid pFS8 (Krone et al., *J. Bacteriol.* 153:716–721, 1983). The iutA gene was subcloned from pFS8 into an Asd+ plasmid vector pYA292 to create pMEGO55 (FIG. 5), and introduced into a Δasd derivative of *S. typhimurium* strain MGN996. Results of western blot analysis indicates that the IutA protein is constitutively expressed and that expression is stable over 50 generations in L broth.

Other outer membrane proteins that may be expressed include the iron-regulated outer membrane proteins, FepA, FecA, FhuA, FecA, and a protein involved in serum resistance, Iss.

All references cited in this specification either supra or infra are hereby incorporated by reference. The discussion of the references herein is intended merely to summarize the assertions made by their authors and no admission is made as to the accuracy or pertinency of the references or that any reference is material to patentability.

What is claimed is:

1. A composition for stimulating an immune response in birds against an avian pathogenic gram-negative ($AP_{G-N}$) microbe selected from the group consisting of *Escherichia coli* serotypes O1, O2, O3, O6, O8, O15, O18, O35, O71, O74, or O78; Salmonella group C strains; Salmonella group D strains; and avian pathogenic species from Bordetella, Haemophilus, Pasturella, Klebsiella, Pseudomonas, or Ornithobacterium, comprising live cells of a recombinant Salmonella strain expressing an O-antigen of the $AP_{G-N}$ microbe against which the immune response is directed, the recombinant Salmonella strain having an rfb/rfc gene cluster of the $AP_{G-N}$ microbe stably integrated into the Salmonella chromosome and having a mutation in the Salmonella rfb gene cluster or in the Salmonella rfc gene which inactivates expression of Salmonella O-antigen, wherein the recombinant Salmonella strain is an attenuated mutant of a virulent Salmonella strain which is capable of colonizing birds.

2. The composition of claim 1, wherein the $AP_{G-N}$ microbe is an avian pathogenic *Escherichia coli* (APEC) strain.

3. The composition of claim 2, wherein the integrated APEC rfb/rfc gene cluster comprises an attenuating mutation in a Salmonella gene selected from the group consisting of pab, pur, aro, asd, dap, nadA, pncB, galE, pmi, fur, rpsL, ompR, htrA, hemA, cdt, cya, crp, phoP, phoQ, rfc, poxA, and galU.

4. The composition of claim 3, wherein the attenuating mutation is a defined deletion/insertion mutation in the Salmonella cya gene.

5. The composition of claim 4, wherein the recombinant Salmonella strain also has an attenuating mutation in the Salmonella crp gene.

6. The composition of claim 5, wherein the APEC strain has a serotype of O1, O2, O35 or O78.

7. The composition of claim 1, wherein the recombinant Salmonella strain also has a recombinant polynucleotide encoding a desired gene product.

8. The composition of claim 7, wherein the desired gene product is an antigen from an avian pathogenic organism.

9. The composition of claim 8, wherein the avian pathogenic organism is an avian pathogenic *Escherichia coli* (APEC) strain and the antigen is a fimbriae or an iron-regulated outer membrane protein of the APEC strain.

10. A method for stimulating an immune response in a bird against an avian pathogenic gram-negative ($AP_{G-N}$) microbe selected from the group consisting of *Escherichia coli* serotypes O1, O2, O3, O6, O8, O15, O18, O35, O71, O74, or O78; Salmonella group C strains; Salmonella group D strains; and avian pathogenic species from Bordetella, Haemophilus, Pasturella, Klebsiella, Pseudomonas, or Ornithobacterium, the method comprising administering to the bird an effective amount of a composition comprising live cells of a recombinant Salmonella strain expressing an O-antigen of the $AP_{G-N}$ microbe against which the immune response is directed, the recombinant Salmonella strain having an rfb/rfc gene cluster of the $AP_{G-N}$ microbe stably integrated into the Salmonella chromosome and having a mutation in the Salmonella rfb gene cluster or in the Salmonella rfc gene which inactivates expression of Salmonella O-antigen, wherein the recombinant Salmonella strain is an attenuated mutant of a virulent Salmonella strain which is capable of colonizing birds.

11. The method of claim 10, wherein the $AP_{G-N}$ microbe is an avian pathogenic *Escherichia coli* (APEC) strain.

12. The method of claim 11, wherein the integrated APEC rfb/rfc gene cluster comprises an attenuating mutation in a Salmonella gene selected from the group consisting of pab, pur, aro, asd, dap, nadA, pncB, galE, pmi, fur, rpsL, ompR, htrA, hemA, cdt, cya, crp, phoP, phoQ, rfc, poxA, and galU.

13. The method of claim 12, wherein the attenuating mutation is a defined deletion/insertion mutation in the Salmonella cya gene.

14. The method of claim 13, wherein the recombinant Salmonella strain also has an attenuating mutation in the Salmonella crp gene.

15. The method of claim 14, wherein the APEC strain has a serotype of O1, O2, O35 or O78.

16. The method of claim 10, wherein the recombinant Salmonella strain also has a recombinant polynucleotide encoding a desired gene product.

17. The method of claim 10, wherein the bird is a chicken or a turkey.

18. The method of claim 17, wherein the composition is administered by coarse spray at day-of-hatch.

19. The method of claim 18, further comprising orally administering to the bird a booster amount of the composition.

20. The method of claim 19, wherein the booster amount is administered on day 13, 14, or 15 after day-of-hatch.

21. A composition for stimulating an immune response in birds against at least two avian pathogenic gram-negative ($AP_{G-N}$) microbes, the vaccine comprising a mixture of live cells of first and second recombinant Salmonella strains, the first recombinant Salmonella strain having an rbf/rfc gene cluster of a first $AP_{G-N}$ microbe integrated into the Salmonella chromosome and expressing an O-antigen of the first $AP_{G-N}$ microbe and the second recombinant Salmonella strain having an rfb/rfc gene cluster of a second $AP_{G-N}$ microbe integrated into the Salmonella chromosome and expressing an O-antigen of the second $AP_{G-N}$ microbe, wherein each of the first and second recombinant Salmonella strains has a mutation in the Salmonella rfb gene cluster or in the Salmonella rfc gene which inactivates expression of Salmonella O-antigen, wherein the first $AP_{G-N}$ microbe and the second $AP_{G-N}$ microbe are selected from the group consisting of *Escherichia coli* serotypes O1, O2, O3, O6, O8, O15, O18, O35, O71, O74, or O78; Salmonella group C or group D strains; and avian pathogenic species from Bordetella, Haemophilus, Pasturella, Klebsiella, Pseudomonas, or Ornithobacterium, and wherein each of the first and second recombinant Salmonella strains is an attenuated mutant of a virulent Salmonella strain which is capable of colonizing birds.

22. A composition for stimulating an immune response in birds against strains of at least two avian pathogenic gram-negative ($AP_{G-N}$) microbes each of which strains is selected from the group consisting of *Escherichia coli* serotypes O1, O2, O3, O6, O8, O15, O18, O35, O71, O74, or O78; Salmonella group C or group D strains; and avian pathogenic species from Bordetella, Haemophilus, Pasturella, Klebsiella, Pseudomonas, or Ornithobacterium, the composition comprising live cells of a recombinant Salmonella strain expressing an O-antigen of each of the $AP_{G-N}$ microbes against which the immune response is directed, the recombinant Salmonella strain having an rfb/rfc gene cluster of each of the $AP_{G-N}$ microbes stably integrated into the Salmonella chromosome and having a mutation in the Salmonella rfb gene cluster or in the Salmonella rfbc gene which inactivates expression of Salmonella O-antigen, wherein the recombinant Salmonella strain is an attenuated mutant of a virulent Salmonella strain which is capable of colonizing birds.

23. A method of making a composition for stimulating an immune response in a bird against an avian pathogenic gram-negative ($AP_{G-N}$) microbe selected from the group consisting of *Escherichia coli* serotypes O1, O2, O3, O6, O8, O15, O18, O35, O71, O74, or O78; Salmonella group C or group D strains; and avian pathogenic species from Bordetella, Haemophilus, Pasturella, Klebsiella, Pseudomonas, or Ornithobacterium, comprising the steps of:
  (a) selecting a Salmonella strain capable of colonizing the bird;
  (b) integrating into the Salmonella chromosome an rfb/rfc gene cluster from the $AP_{G-N}$ microbe against which the immune response is directed;
  (c) introducing a mutation into the Salmonella rfb gene cluster and/or into the Salmonella rfc gene; and
  (d) isolating recombinant Salmonella bacteria which express O-antigen characteristic of the $AP_{G-N}$ strain but which do not express Salmonella O-antigen, wherein steps (b) and (c) can be performed in any order.

24. The method of claim 23, wherein the selected Salmonella strain is an attenuated mutant of a virulent Salmonella strain.

25. The method of claim 24, wherein the selected Salmonella strain is a virulent Salmonella strain and the method further comprises introducing into the virulent Salmonella strain an attenuating mutation in a Salmonella gene selected from the group consisting of pab, pur, aro, asd, dap, nadA, pncB, galE, pmi, fur, rpsL, ompR, htrA, hemA, cdt, cya, crp, phoP, phoQ, rfc, poxA, and galU, and then isolating mutants having attenuated virulence as compared to the virulent Salmonella strain.

26. The composition of claim 1, wherein the mutation which inactivates expression of Salmonella O-antigen is a mutation in the Salmonella rfb gene cluster.

27. The method of claim 11, wherein the mutation which inactivates expression of Salmonella O-antigen is a mutation in the Salmonella rfb gene cluster.

28. the method of claim 25, wherein step (c) comprises introducing a mutation into the Salmonella rfb gene cluster.

29. The composition of claim 26, wherein the recombinant Salmonella strain also has a recombinant polynucleotide encoding a desired gene product.

30. The composition of claim 1, wherein the recombinant Salmonella strain is selected from the group consisting of *Salmonella typhimurium, Salmonella enteriditis, Salmonella heidelberg, Salmonella gallinorum, Salmonella hadar, Salmonella agona, Salmonella kentucky* and *Salmonella infantis.*

* * * * *